(12) United States Patent
Boeckle

(10) Patent No.: US 9,126,122 B2
(45) Date of Patent: Sep. 8, 2015

(54) DOLL COMPANION INTEGRATING CHILD SELF-DIRECTED EXECUTION OF APPLICATIONS WITH CELL PHONE COMMUNICATION, EDUCATION, ENTERTAINMENT, ALERT AND MONITORING SYSTEMS

(75) Inventor: Thomas T. Boeckle, Las Vegas, NV (US)

(73) Assignee: ZUGWORKS, INC, Las Vegas, NV (US)

( * ) Notice: Subject to any disclaimer, the term of this patent is extended or adjusted under 35 U.S.C. 154(b) by 480 days.

(21) Appl. No.: 13/109,993

(22) Filed: May 17, 2011

(65) Prior Publication Data

US 2012/0295510 A1    Nov. 22, 2012

(51) Int. Cl.
  *A63H 3/00*   (2006.01)
  *A63H 3/28*   (2006.01)
  *G09B 5/06*   (2006.01)

(52) U.S. Cl.
  CPC .. *A63H 3/28* (2013.01); *G09B 5/06* (2013.01); *A63H 2200/00* (2013.01)

(58) Field of Classification Search
  CPC ......... A63H 3/28; A63H 2200/00; G09B 5/06
  USPC ................................... 446/72, 268, 297, 484
  See application file for complete search history.

(56) References Cited

U.S. PATENT DOCUMENTS

| 5,746,602 | A | 5/1998 | Kikinis |
| 5,752,880 | A | 5/1998 | Gabai et al. |
| 5,873,765 | A | 2/1999 | Rifkin et al. |
| 6,169,477 | B1 * | 1/2001 | Fiato ............................. 340/326 |
| 6,250,557 | B1 * | 6/2001 | Forslund et al. .............. 235/492 |
| 6,494,762 | B1 * | 12/2002 | Bushmitch et al. ........... 446/268 |
| 6,773,344 | B1 * | 8/2004 | Gabai et al. ....................... 463/1 |

(Continued)

FOREIGN PATENT DOCUMENTS

CN    101404677    4/2009
JP    2008077465 A    8/2004

(Continued)

OTHER PUBLICATIONS http://www.mobile88.com/cellphone/I-Care/I-Care-Kids-Mobile/review.asp—I-Care Kids Mobile Phone.

(Continued)

*Primary Examiner* — Alvin Hunter
*Assistant Examiner* — Joseph B Baldori
(74) *Attorney, Agent, or Firm* — Connie R. Masters

(57) ABSTRACT

The presented cell phone-enabled doll companion allows a child novel ways to self-select and self-execute applications while requiring no intervention or supervision from the parent. Further, it provides learning, entertainment and safety by integrating cell phone communication, education, entertainment, alert and monitoring systems. While providing a convenient means of communication between the child and parent, the system allows surveillance of a child's real-time environment, GPS monitoring and SIDS/health monitoring. The functionality and the physical elements of the system are programmable through installation of applications downloadable from an application store. Various options for parental access to a configuration interface to modify settings and download applications are provided, including via a cell phone, a website, customer service call center and/or the doll companion touch screen.

13 Claims, 26 Drawing Sheets

(56) References Cited

U.S. PATENT DOCUMENTS

| | | | |
|---|---|---|---|
| 6,838,998 | B1 | 1/2005 | Brown et al. |
| 6,847,892 | B2 | 1/2005 | Zhou et al. |
| 7,005,999 | B2 | 2/2006 | Salzhauer et al. |
| 7,008,288 | B2 | 3/2006 | Covannon et al. |
| 7,009,522 | B2 * | 3/2006 | Flanagan et al. ............ 340/666 |
| 7,353,034 | B2 | 4/2008 | Haney |
| 7,627,451 | B2 | 12/2009 | Vock et al. |
| 7,821,392 | B2 | 10/2010 | Brown |
| 2002/0128746 | A1 | 9/2002 | Boies et al. |
| 2004/0155775 | A1 | 8/2004 | Kaneko |
| 2004/0198382 | A1 | 10/2004 | Wong |
| 2005/0176461 | A1 | 8/2005 | Bozzone et al. |
| 2006/0028346 | A1 | 2/2006 | White |
| 2006/0079147 | A1 * | 4/2006 | Wong et al. ............ 446/142 |
| 2007/0242661 | A1 | 10/2007 | Tran |
| 2008/0062120 | A1 | 3/2008 | Wheeler et al. |
| 2009/0055019 | A1 | 2/2009 | Stiehl et al. |
| 2009/0197504 | A1 * | 8/2009 | Hsu ............................ 446/301 |
| 2010/0164712 | A1 | 7/2010 | Corrigan |
| 2010/0274104 | A1 | 10/2010 | Khan |
| 2011/0021109 | A1 * | 1/2011 | Le et al. ................ 446/300 |
| 2013/0040530 | A1 * | 2/2013 | Matsuno ................... 446/73 |

FOREIGN PATENT DOCUMENTS

| | | |
|---|---|---|
| JP | 2010067169 A | 9/2008 |
| KR | 20040022314 A | 3/2004 |
| WO | WO0169799 A2 | 3/2001 |
| WO | WO2004059996 A1 | 7/2004 |
| WO | WO2006108071 A2 | 10/2006 |
| WO | WO2010125338 A1 | 11/2010 |

OTHER PUBLICATIONS http://chinagrabber.com/browseproducts/01PC-1.3--Flip-Open--Gucci-PUCCA--Doll-Phone-w--Bluetooth--Camera---G99i.html, Gucci-Doll G99i Pucca phone With Camera & Bluetooth.
www.beebuyer.com/ .../157917-Imobile-Phone Imobile Phone V226—GSM 900 /1800 mHz.
http://www.wi-ltd.com/safety/Child_Patient_Monitoring/Baby_Monitoring/GSM_Wireless_Baby_Monitor_V900B—GSM Wireless Baby Monitor V900B.
http://www.garminasus.com/en_US/phones/garminfone/—Garminfone—Overview~Garmin-Asus.
www.garmin.com—NavTalk.
https://www.amberalertgps.com/products/gps_tracking/amber_alert_gps_3g/—Amber Alert GPS™ Armor.
Nu•m8 User Guide by Hana Microelectronics Ltd.
http://www.lok8u.com/us—lok8u.
http://www.securatrac.com/lifetrac/—SecuraTrac.
www.brickhousesecurity.com/child-locator—Child Locator by BrickHouse Security.
Burnside Easy Answer Datasheet P235 by Burnside Telecom Ltd—www.burnsidetelecom.com.
GSM Wireless Baby Monitor V900B, Westminister.
Written Opinion of the International Searching Authority, Korean Intellectual Property Office.
International Search Report, Korean Intellectual Property Office.

* cited by examiner

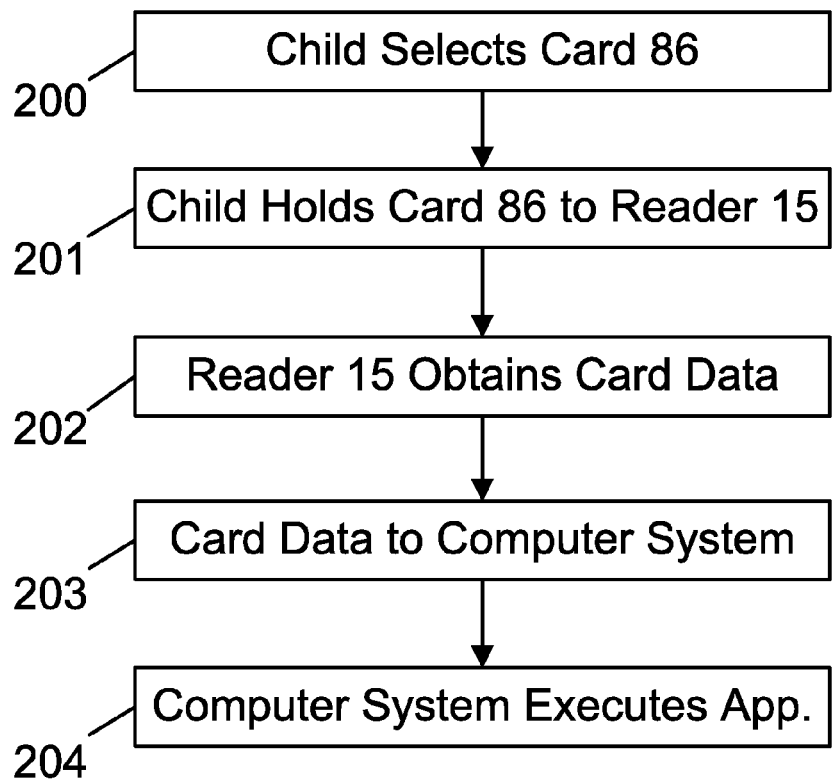
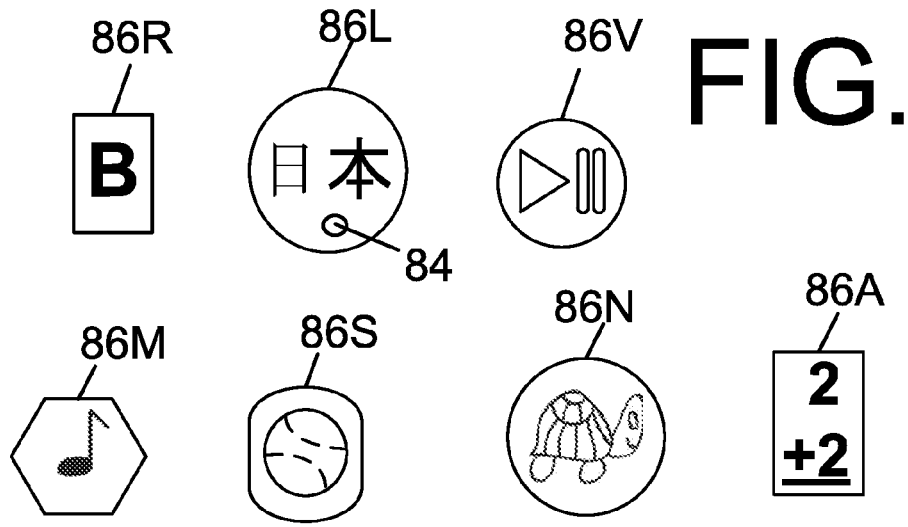

Representative Card 86

Individual Card 86

Corresponding Card 86

Child Input 45

Parent Access 299

Systems Configuration

Integrated Systems

Alert System 120

Alert System 120 Configuration 900

Local Audio System 90A

Local Audio/Visual Sys. 90B

Cell Audio/Visual Sys. 130

GPS Systems 60 Components

Health/SIDS System 70

Heath/SIDS Sys. 70 Components

Health/SIDS System 70 Config. 950

Education 80
Entertainment 110
Systems

Education 80
Entertainment 110
Components

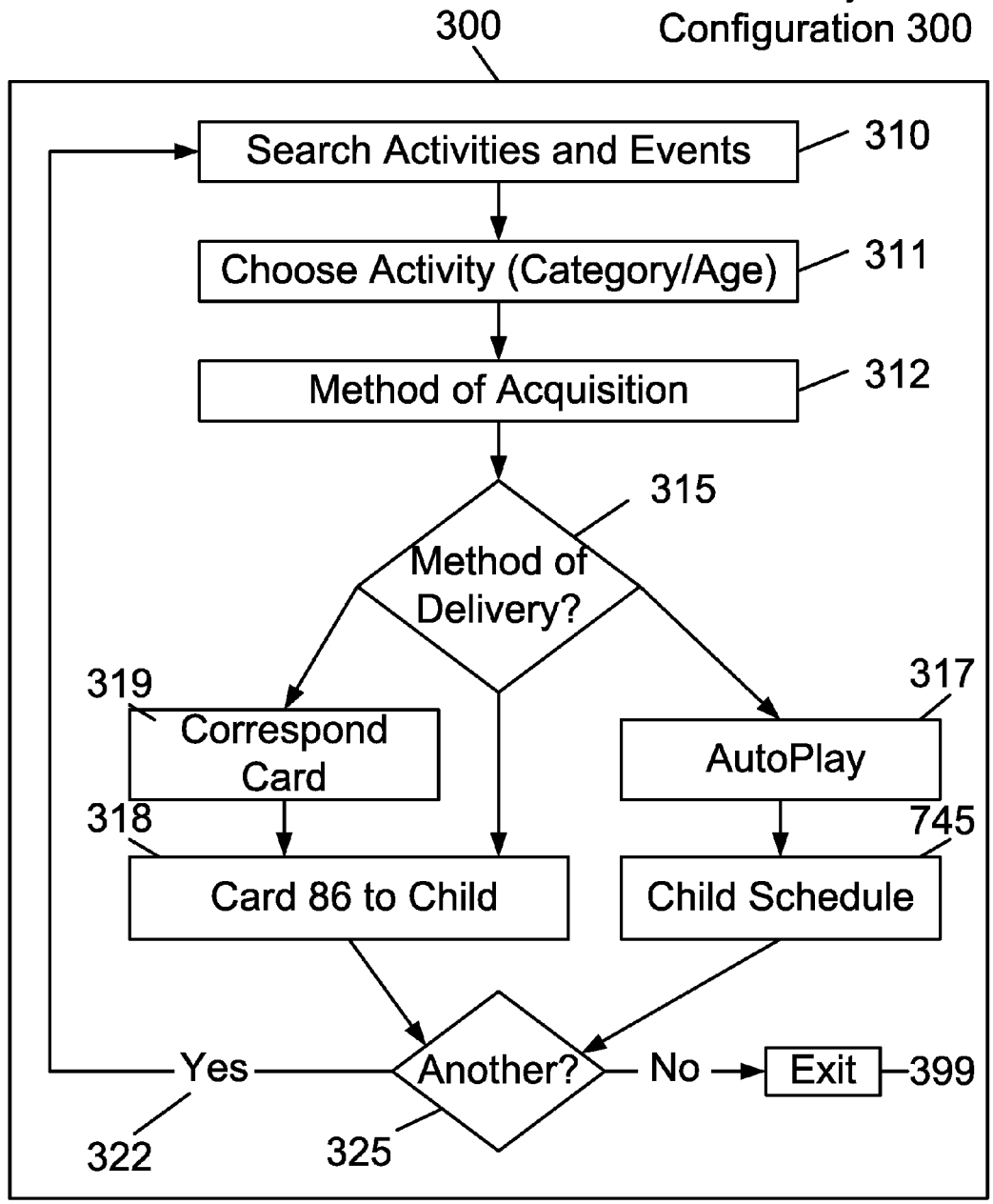

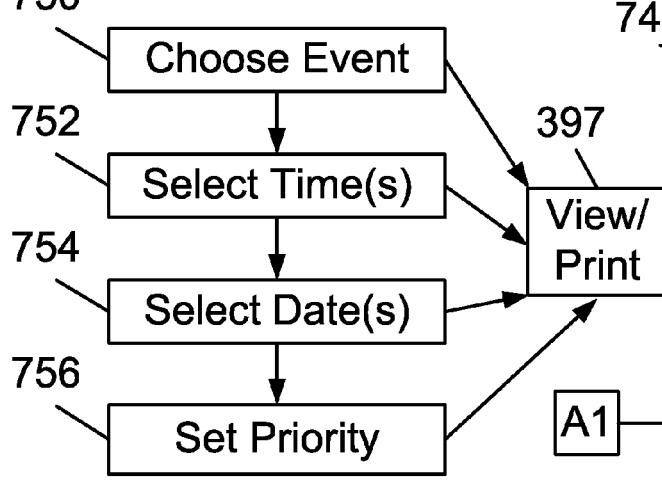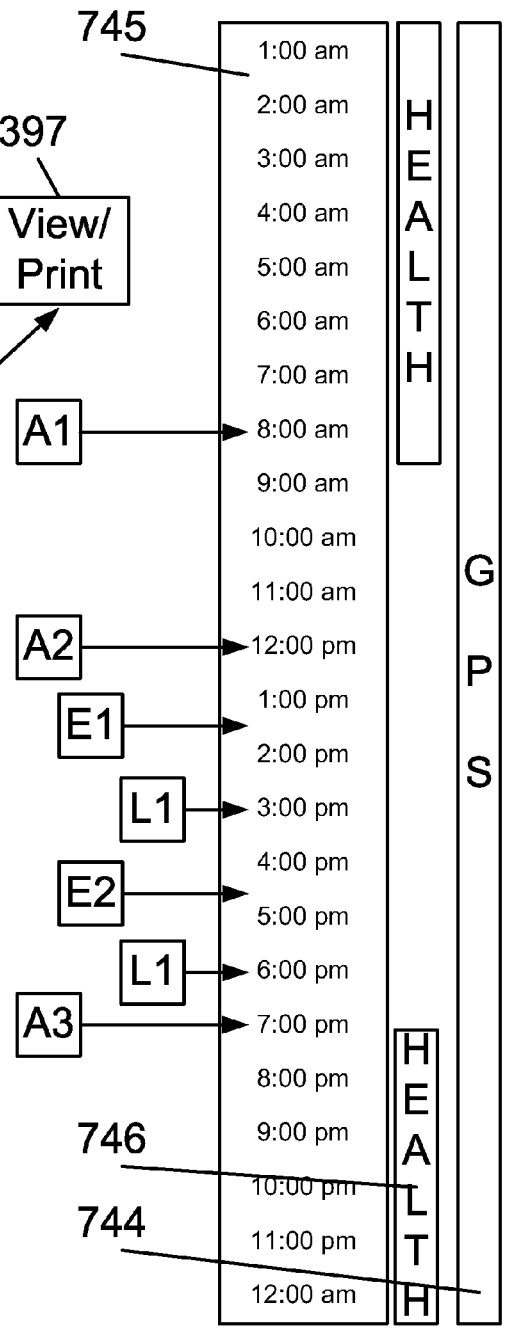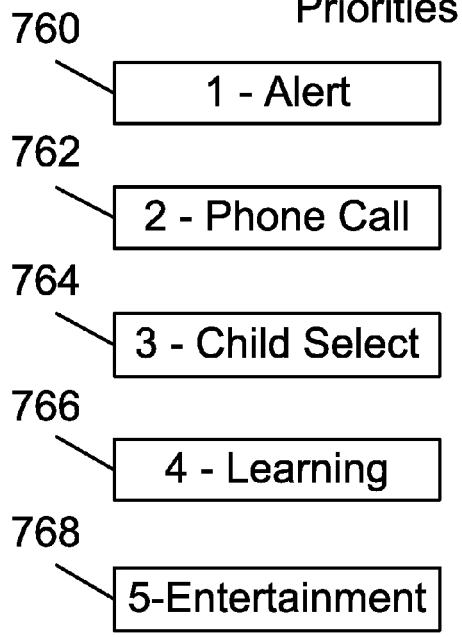

DOLL COMPANION INTEGRATING CHILD SELF-DIRECTED EXECUTION OF APPLICATIONS WITH CELL PHONE COMMUNICATION, EDUCATION, ENTERTAINMENT, ALERT AND MONITORING SYSTEMS

FIELD OF THE INVENTION

The present invention relates generally to a cell phone-enabled doll companion, and more particularly, to a doll companion allowing a child to execute applications and allowing a parent to configure the integrated cellular communication, education, entertainment, alert and monitoring systems.

BACKGROUND INFORMATION

Children are often given toys that perform actions or activities planned to provide educational or entertainment benefits. Often the child can turn the toy on and turn the toy off, but has little control of the presentation of the activity or control over the actions the toy is programmed to perform—the toy carries out the pre-planned functions. Nor can the child select which activity or action is to be performed.

Though children's educational software is available that allows an older child to use mouse and keyboard to control an activity, the computer-mouse-keyboard interface is not usable by a younger child. Also, some children do not have consistent access to a computer. Some parents prefer not to allow the child to use a computer due to security concerns. Some software does not engage the child's attention or cannot be adjusted to meet the child's changing needs. Many children's learning programs are not readily available to the parent or child, particularly compared to the quickly and easily available applications offered for immediate download in applications stores. Therefore currently available educational software does not fully meet the needs of the child.

Additionally, a younger child who cannot read cannot execute an activity, which entails choosing a CD ROM, inserting it appropriately into the computer and navigating through the displayed screen prompts to execute the selected activity; the child requires parental assistance. Children like to make their own choices and control their own environment; yet currently available systems do not allow self-directed selection, control and execution of activities by the younger child. Thus, there is a need for a workable system that lets the younger child self-select an activity, self-execute that activity, and control the functions of that activity without requiring help from the parent.

The care, safety and education of a child are top parental priorities. Numerous monitoring and education/entertainment systems have been developed to assist the parent in meeting these goals, yet each is lacking in some feature or aspect. For example, though monitoring alert systems can warn or alert a parent, they do not allow efficient real-time voice and video communication between the parent and child. For instance, if the child is lost, a conventional GPS alert system may notify the parent that the child has wandered off, but will not allow the parent to see there is a picnic table beside the child and, then, to say to the child, "See the red picnic table in front of you? Sit there and wait. I will come right away."

Also, conventional monitoring systems are generally standalone systems, adding to the large number of varied electronic devices that must be managed, configured, charged and carried by the parent.

Commonly available child monitoring systems include audio and audio-video monitoring systems that receive input from the baby's room and transmit it to a portable audio receiver device. Though the parent in a nearby room is able to hear if a child calls out or cries, these systems are not designed to allow a remote parent (across town or across the country) to monitor a child. Though some monitoring systems can be connected to a home network Internet connection to allow remote parental surveillance from an Internet-connected computer, the complicated setup involving port forwarding and other advanced networking tweaks will deter many potential users—or will necessitate the expense of hiring a network technician. Additionally, these monitoring systems are one-way systems and do not allow two-way communication and interaction between the parent and the child. For example, though the parent at his office computer may be able to see that the child at home is about to pull a pot of boiling water off the stove, he cannot give a real-time voice warning.

Other child monitoring systems are focused on using GPS technology to determine the location of a child. A few of these GPS monitoring systems make partial use of a cellular phone network. For example, the Amber Alert GPS (shaped like a small plastic pod) and the SecuraPAL® Guardian personal locator (shaped like a candy bar style cell phone) are commercially available cellular phone-enabled GPS tracking devices. Both allow the parent to log onto an online application to see recent or previous locations of the child and to manage alerts (text, email or phone). The Amber Alert GPS device can also serve as an audio monitor; the parent calls the device and is automatically connected to listen to the child's environment without notifying the child that audio monitoring has been activated. Similarly, the Nu-M8 tracking device (based on PCT WO 2010/125338 by Bentley) incorporates both cellular transmission and GPS tracking within a bracelet or wristband format, which must necessarily be small to be usable by very small children. The Nu-M8 tracking device attempts to overcome the technical difficulties of the joint cellular and GPS transmissions, of maintaining sufficient battery power to run the device, and of calculating location coordinates in light of the limited computational and battery power in such a small wristband device. However, these GPS tracking devices do not provide efficient parent-child communication. Plus, the child may not be cooperative, as wearing the wristband or carrying the tracking pod is troublesome without an apparent gain from the child's point of view. Additionally, this type of standalone system adds yet another electronic device to the parent's collection of family electronic devices to manage, with inherent monetary costs and time costs (learning to use the device, keeping the device charged, maintaining the device and the like).

Another type of monitoring system, used to detect Sudden Infant Death Syndrome (SIDS), has a sensor for monitoring health parameters and a transmission method. For example, in US Patent Application Publication US2010/0274104 by Khan, a monitor is attached to a band worn by a child and configured to transmit an alert if the measured parameters are outside of the pre-set parameters. Various communication interfaces are discussed, including transmission of the alert by cellular and Internet communications. However, the device does not provide efficient communication between the parent and child, nor does it have entertainment or educational benefits. Further, the size of the device must be minimized to be worn on the wrist of a child so the size of the battery is small, necessitating frequent charging.

To allow communication between a remote parent and a child, various systems using cellular communication have been developed. Young children cannot manage the complexities of cell phones that sometimes even challenge adult users. Simplified cell phones for children have been developed, such as a commercially available rigid I-Care™ plastic bear-shaped mobile phone with seven buttons. Though it simplifies dialing by having four pre-set buttons (such as mother, father, friend and teacher) and an SOS button, it additionally requires the usage of a call out and hang up button, so appears to only be suitable for children of kindergarten age and older. Additionally, the I-Care mobile phone provides auto-answering to allow the parent to listen to the child's environment. The SecuraPAL® Guardian personal locator discussed above includes a single pre-set speed dial button. Similarly, in China Patent Application No. 200810068428 by Chen, a child's mobile phone with GPS that has a battery-powered motor for moving the limbs, head and mouth is presented. The toy- or pet-shaped mobile phone has a left hand button ("Mommy"), right hand button ("Daddy"), right foot button ("teacher") and left foot button ("police"), which can be pre-set with dial out numbers by text message. Though the Chen phone uses the cellular system, it cannot be configured by the parent, except by the limited text message function. Certainly, the child cannot self-direct learning or entertainment, as the Chen phone does not incorporate learning or entertainment options for the child.

Communication between a parent and a child can also be provided by computer-connected doll systems. These generally allow the parent to mechanically control a portion of a doll. For example, a parent at a computer in the same room as the child may move the doll's arm to make it appear that the doll is interacting with the child. Kikinis, U.S. Pat. No. 5,746,602 filed in 1996, covers a doll connected to a computer that can tell stories, teach languages, play music, and offer other educational options, as chosen by the parent at the computer primarily by inserting a CD ROM into the computer to execute the desired program, which then activates and/or animates the doll. The Kikinis doll is substantially a computer interface designed for a child, but is limited in its lack of a method to allow the child to select programs, and by its limitation of computer tethering.

Gabai, U.S. Pat. No. 5,752,880, covers the controlling of a doll wirelessly by radio transmission through a computer. A program running on the computer issues a command to a toy, the toy performs the command, and the toy then provides feedback to the computer that it has performed the command. In PCT Application No. WO01069799 filed in 2001, Gabai expanded his computer-controlled doll system to an Internet-controlled doll system having a network-mediated toy-controlling data communication link for controlling aspects of the toy; other optional devices to allow connections to remote computers are mentioned, such as television set-top boxes, cable networks, base station, cellular phone and telephone line connections. Obtaining the correct equipment and setting up this networked situation may not be straightforward. Additionally, this system requires an Internet connection and a means to connect to it, which are not always available. Furthermore, the child cannot self-direct learning or entertainment.

Smart toys have attempted to address the desire for better children's educational systems, but the modes of interaction between a child and the smart toy are not well developed. For example, some references present a smart toy that uses language recognition software, so that children can manage the content they want by speaking to the toy. The limits of this are obvious, however, as even adults suffer from extreme frustration with automated voice answering systems that barely work. Other smart toys involve many cartridges and corresponding books that must be kept together and well maintained to be usable.

One of the more advanced smart toys is presented in U.S. patent application Ser. No. 12/117,389 by Stiehl, et al., assigned to MIT, and is titled "Interactive Systems Employing Robotic Companions." The principal device of the system is a robot in the form of a plush doll, preferably, a teddy bear called the "Huggable" in the patent application. The Huggable has a motor and interior working mechanism to move its head, arms, etc. Its overlay is a soft material imitating skin and fur. It is outfitted with sensors or air bladders that enable the Huggable to "feel." The Huggable's eyes are cameras for video streaming; and it has a microphone and speakers enabling it to hear and speak. Through a web-page implementation of control, the Huggable allows interaction with a remotely-located person, where the user of the robot has a relationship with a remotely located person such as a teacher (foreign language teacher, math tutor, etc.) or a relative (parent, grandparent, etc.) and the remotely located person (known as a "puppeteer") controls the robot. Though the Huggable plush toy allows viewing, hearing and communicating with a child remotely and provides a means to connect remote relatives and teachers through the Internet, it is tied to Internet connectivity due to the real-time manipulation of the controls of the robot, so cannot take advantage of the benefits of cell phone connectivity, such as a more developed and pervasive communication network, a different price structure, different communication capabilities, etc. Additionally, it does not include security features and does not allow child-directed control or learning.

Cell phones have become ubiquitous, with younger and younger children declaring their yearning for a personal cell phone. Yet conventional cell phones are not adapted to meet the needs of younger children; protocols are not developed to meet the needs of the child and parent. Also, children cannot select the content they want nor execute the programs needed to deliver this content.

Additionally, the number of individual electronic devices specialized for one function continues to grow and expand. The large number of electronic devices normally owned increases clutter and decreases optimum usage. The learning curve to use each one effectively often prevents efficient use. Maintenance, keeping accessories located, and charging of the devices takes precious time from the parent.

Accordingly, while numerous educational toys and monitoring systems have been developed, and while conventional cell phones are readily available, there is an established need for a child-oriented doll companion that allows the child self-directed access to, and selection of, the functionality and applications of the system. The system further advantageously integrates cell phone communication, education, entertainment, alert and monitoring systems in a way that allows convenient usage by the parent (configuration of settings, planning of a daily learning and entertainment schedule for the child, and communication).

SUMMARY OF THE INVENTION

The present invention is directed to a doll companion integrating child self-directed execution of applications with a cell phone system, monitoring systems, an educational system, an alert system and an entertainment system into a compact, portable single entity, the cell-enabled integrated learning system, referred to herein as the "CEIL" system. The CEIL system incorporates all of the functions and advantages of a smart cell phone that is easily modifiable and expandable with downloaded applications, plus adds the advantages of the other integrated systems. Significantly, the present invention is equipped with novel means enabling even young toddlers to self-execute educational and entertainment applications. If an 11-month old toddler wants to see her video of a mother duck and babies, she can select the smart card showing a picture of the duck family, hold it up to the card reader within the doll companion, and play that video. Or to play a matching colors game, she can hold a unique, colored smart card up to the doll companion and, without her parents' help, execute that application.

During the day, the doll companion may make cute sounds in response to the toddler's vocalizations. Or the doll companion may be configured to repeat each word the child says in Spanish, thereby effortlessly teaching a second language. Hence, the doll interacts with and responds to the child; the bond and affinity that develop between the child and the doll companion causes the child to desire to keep the doll near, facilitating monitoring by the parent.

Additionally, with or without access to a computer, a variety of parent-friendly configuration interfaces allow convenient configuration of the settings of the various systems, allow downloading of applications to expand entertainment and education, enable the parent to establish protocols appropriate for the age and abilities of the child, and permit the parent to set up and modify a daily learning, entertainment and alert schedule for the child. Through use of the downloaded applications, configuration interface and child-selectable inputs, the CEIL system can be customized for the child at his current age and ability, plus the CEIL system can be altered as needed to meet the changing needs of the child as he learns and grows. Advantageously, the configuration interface can be accessed, the configuration settings can be updated, and applications can be downloaded into the CEIL system with or without a computer connection. The parent can access the configuration interface through a computer-based system with the doll companion connected to the computer, through a web-based system from a remote parent's computer or smart phone, by assistance from a customer service call center, by voice commands, and through use of text commands.

The cell phone system provides remote communication between the child and parent or other approved contact. ("Parent" is herein used to include one or both parents, legal guardians, nannies, caregivers and other custodial adults who have responsibility for the child.) Using the cellular connectivity or, optionally, a presented local system, the parent is also provided with a means of viewing and hearing a child's real-time environment. The integrated education and entertainment system provides opportunities to teach, engage, amuse, develop skills and provide instruction to young children. The integral alert system allows the parent to give alerts, alarms, schedule information and guidance to the child. The optional GPS security feature allows the parent to set limits and track the child's location. When using the optional health/SIDS monitoring safety feature, the parent or authorized medical provider can verify aspects of the child's health, thus providing reassurance and peace of mind.

An object of the present invention is to provide a cell phone-enabled CEIL system that provides means for the child to select and execute an application.

Another object of the present invention is to provide a cell phone-enabled CEIL system that allows a remote parent to view and hear a child's environment in substantially real time via cellular connectivity.

A further object of the present invention is to provide a cell phone-enabled doll companion system that allows the remote parent to communicate with the child via a cell phone system.

An additional object of the present invention is to provide a cell phone-enabled CEIL system that allows the child to interact with the doll companion system.

Another object of the present invention is to provide a cell phone-enabled CEIL system that allows the parent to set up, administer and modify the configurations and protocols of the various systems.

A further object of the present invention is to provide a cell phone-enabled CEIL system that allows the parent to create and manage a daily schedule for the child incorporating entertainment and educational content.

An additional object of the present invention is to provide a cell phone-enabled CEIL system that is operative to provide instruction to the child.

These and other objects, features and advantages of the present invention will become more readily apparent from the attached drawings and from the detailed description of the preferred embodiments, which follow.

BRIEF DESCRIPTION OF THE DRAWINGS

The preferred embodiments of the invention will hereinafter be described in conjunction with the appended drawings, provided to illustrate and not to limit the invention, where like designations denote like elements, and in which:

FIG. 4 is a schematic of the app-initiating smart card system 85 of the doll companion of the present invention;

FIG. 5 shows exemplary types and categories of smart cards of the smart card system 85 of the doll companion of the present invention;

FIG. 37 is a schematic showing an exemplary configuration interface for configuring the educational system or entertainment system of the doll companion system of the present invention;

FIG. 38 is a schematic showing steps in configuring the child's schedule of the doll companion system of the present invention;

FIG. 39 is a schematic showing default priorities of events input into the child's schedule of the doll companion system of the present invention; and FIG. 40 is a schematic showing configuration of the child's schedule of the doll companion system of the present invention.

Like reference numerals refer to like parts throughout the several views of the drawings.

DETAILED DESCRIPTION OF THE PREFERRED EMBODIMENTS

Figure 1:
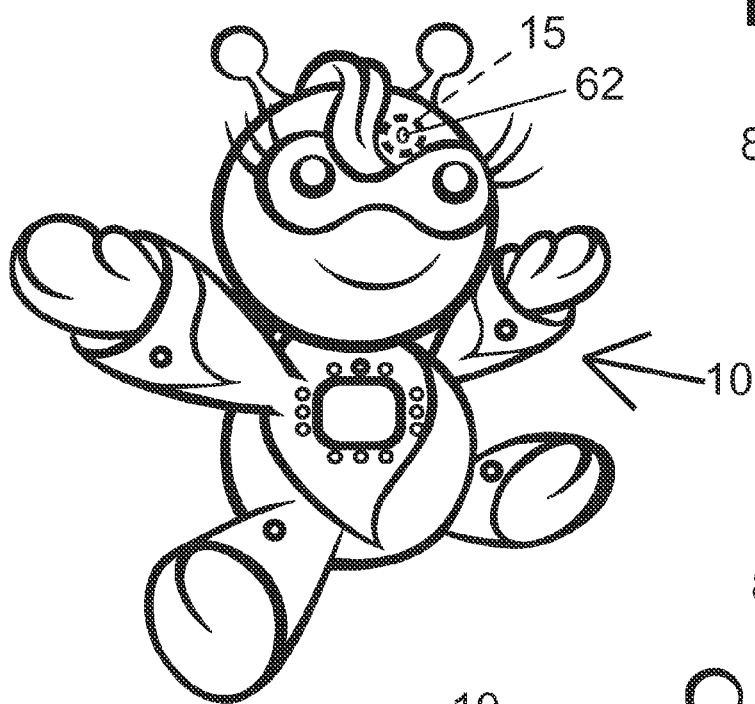
FIG. 1 is a perspective showing the doll companion of the present invention integrating child self-directed execution of applications with cell phone communication, education, entertainment, alert and monitoring systems.

Shown throughout the figures, the present invention is directed toward a child's toy or doll companion integrating child self-directed execution of applications with cellular communication, education, entertainment, alert and monitoring systems to form the novel "cell-enabled integrated learning system" ("CEIL system"), also referred to as the "doll companion." Additionally, a parent configuration interface is provided allowing the parent to customize the CEIL system for the child's needs (including configuring, updating, downloading new content, and establishing a learning, entertainment and alert schedule for the child).

1. Child Self-Directed Selection, Execution, and Control of Applications

The child can interact with and control his CEIL doll companion. The child can choose the game he wants to play, the animation he wants to watch, or call his parent from his bed because he is scared or sick. The CEIL system provides multiple input means for even a young child to select, execute and control applications, without the parent's assistance.

These self-directed, child-activated input devices 45 (FIG. 13), usable separately or in combination, include a smart card system 85 (FIGS. 1-3), tactile buttons 21 (FIGS. 3, 9, 10, 12), and a touchscreen 25 (FIGS. 3, 12) for relatively older children who are comfortable using such screens to make programming selections. In a significant departure from prior art devices and novel improvement over them, the present invention features both "smart cards" (application-initiating cards functional with a card-doll communication interface) and "tactile buttons" (push buttons, levers, knobs, pull handles, joysticks, switches or other child-engagable tactile controls) that are suitable for use by very young children who do not yet use touch screens. For example, an eleven-month-old infant can hold a smart card with a picture of a turtle (smart card 86 of FIG. 2) up to a card reader 15 (FIG. 1) to watch animated turtles dance. An early elementary student will be able to use the displayed interface on the interactive touchscreen 25 to activate and play games on the screen 25. A toddler can easily push the single "push to talk" button 21X, FIG. 18, to tell his parent that his stomach hurts. Or a toddler can execute an application using the application-associated smart card system 85, and then use the tactile buttons 21 to respond to on-screen 25 communication.

In contrast to previous systems, such as the computer-controlled or parent-controlled smart dolls of the cited references, the CEIL system allows the child to self-select and self-initiate activities and communication, including executing learning and entertainment activities and phoning out to his parent through cell phone communication.

Figure 2:
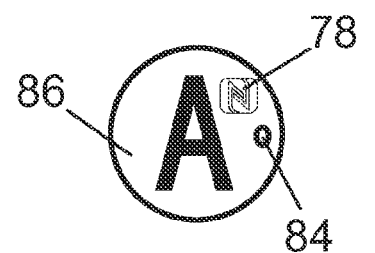
FIG. 2 is a front view of an app-initiating smart card of the present invention configured to allow a young child to execute applications on the doll companion system.
Figure 3:
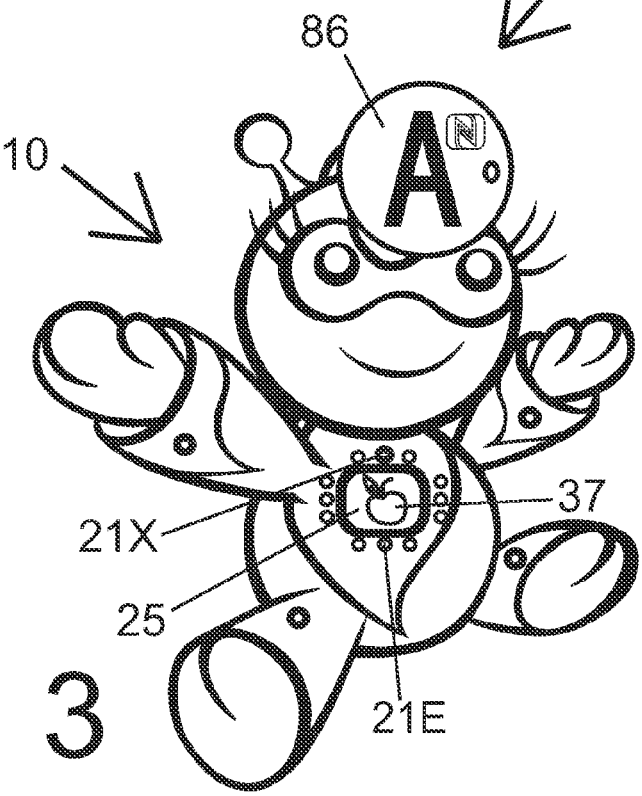
FIG. 3 is a perspective showing the doll companion of the present invention with the smart card executing an application on the doll companion system.

1.1 Application-Initiating Smart Card System FIGS. 1-3

The smart card system 85 includes a card reader 15 operably connected to the CEIL computer system and incorporated in any suitable location within the doll/toy housing 10 of the doll companion. The smart card system 85 also includes a card 86 having stored application-associated data readable by the card reader 15. In certain embodiments, the smart card system 85 further includes an indicator marker 62.

The smart card system 85 allows a young child to execute computer applications of his choice on the CEIL system. The child merely selects the small, portable smart card 86 (FIG. 2) that represents the application he wishes to "play" and interacts the smart card 86 with the card reader 15 (FIG. 1). This is shown in FIG. 3 with the card 86 being placed directly in front of the reader 15, which, in this example, is located in the head of the doll/toy housing 10. The computer system then executes ("plays") the associated application.

For example as shown in FIG. 4, the child selects 200 the "A" alphabet card 86. The child then holds 201 the card 86 to the area of the toy/doll housing 10 enclosing the reader 15. An indicator marker 62 may be positioned externally of the reader 15 to assist the child in bringing the card 86 into the proper position. The reader 15 then obtains 202 the data from the card 86, with the data transmitted 203 to the computer system. The computer system executes 204 the application associated with the particular card. In this example, the "A" alphabet card 86 is associated with an animation 37 (FIG. 3) of objects starting with the letter "A", preferably with correlated songs or other audio. Thus, the smart card system 85 provides a child-friendly computer interface for executing applications, thereby allowing self-directed learning and entertainment at a young age.

Preferably the smart card 86 is a non-positional, non-contact card with application-associated data embedded upon or within the card. The application-associated data comprise a unique ID number, code, or other data that are, or can be, associated with or related to an application 100 and which can be received by the card reader 15. The card reader 15 is operable to read the complementary smart cards 86. The card reader 15 is operably connected to relay the smart card information to the computing system 40 to execute the designated application. Any of a variety of contact or contactless card technologies that are known in the art, or become known, may be used to implement the information transfer between the smart card 86 and the card reader 15.

In a preferable aspect, the smart card system 85 uses contactless technology to accommodate the child's limited dexterity and to increase the ease of use. The contactless smart card 86 needs merely to be held or waved briefly within the connecting distance of the card reader 15. Contactless card technologies include memory cards (passive cards that store data but do not process information), optical cards (that require a laser to read and write data on the card), proximity cards, Near Field Communication (NFC) cards, RFID tags and integrated circuit (IC) cards using radio frequency transmission and having an embedded IC chip that can store and process data.

Preferably, the smart card system 85 uses a short-range wireless NFC technology interface 78 to communicate the application-associated data of the card 86 to the reader 15. The NFC interface meets established standards defining data formats, bandwidth, transmission, etc. NFC typically requires a distance of only a few centimeters, such as around two to four centimeters. Thus, with the reader 15 positioned in the head of the doll companion, as shown in FIG. 1, the child would wave the smart card 86 within a very few centimeters of the forehead, as shown in FIG. 3. Because the NFC interface 78 may permit communication at a very short range, the location of the NFC interface in the reader 15 may be indicated on the exterior of the toy/housing 10, such as by use of indicator marker 62 (FIG. 1), to assist the child in bringing the card 86 within range of the reader 15.

The NFC interface may comply, for example, with such standards as ISO 18092 or ISO 21521, or it may comply with the TransferJets protocol. The NFC interface may typically operate at 13.56 MHz and at rates ranging from 106 Kbit/s to 848 Kbit/s. The close range communication with the NFC interface 78 may take place via magnetic field induction, allowing the reader 15 to communicate with the card 86 NFC interface 78 or to retrieve information from cards having radio frequency identification (RFID) circuitry. The NFC interface 78 may provide a manner of initiating or facilitating a transfer of application-associated data from the card 86. Preferably, the reader 15 is the initiator and actively generates a radio frequency (RF) field that powers the passive target, smart card 86. This allows the smart card 86 to take a simple form factor, removing the need for batteries or charging.

Figure 18:
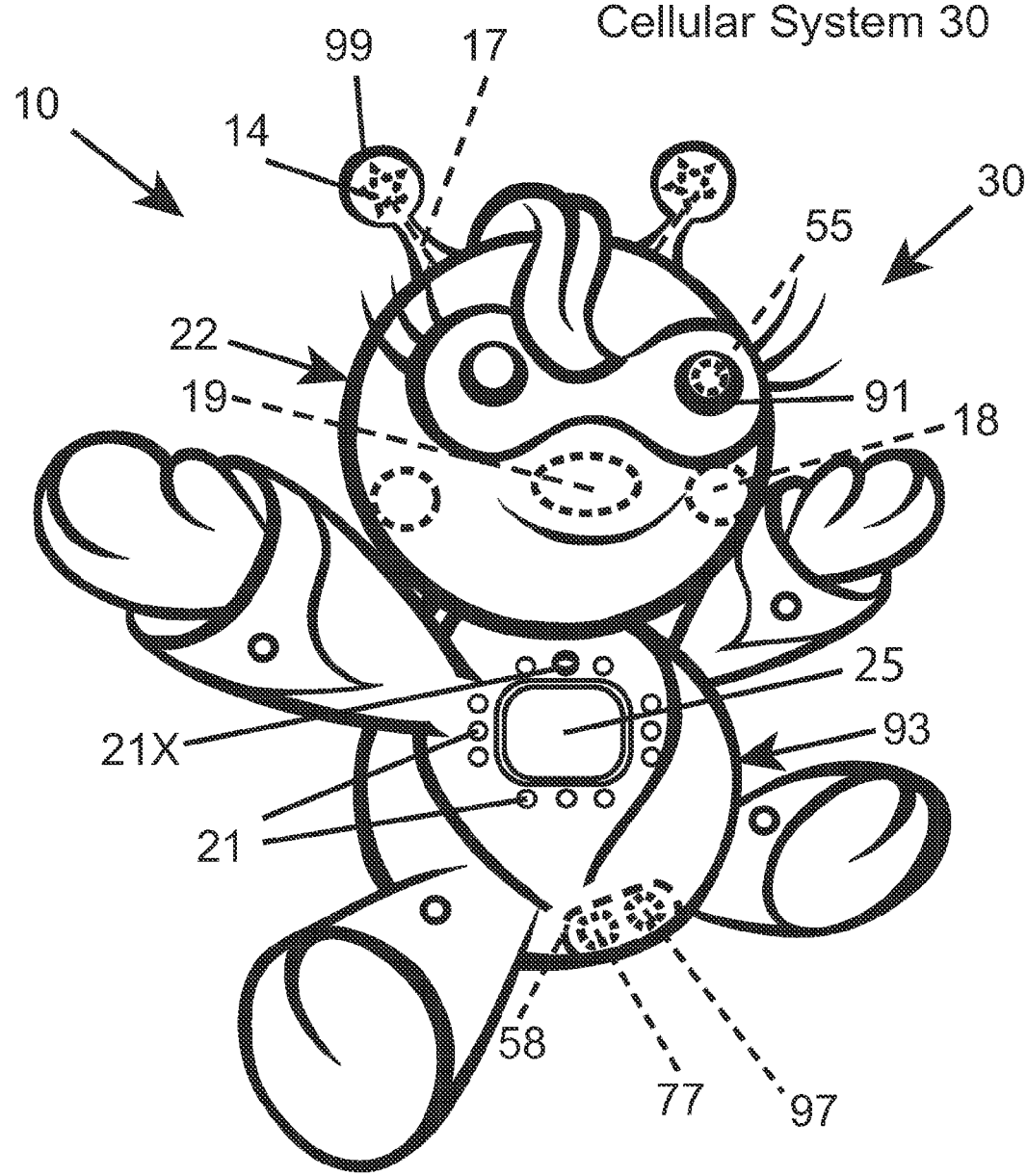
FIG. 18 is a perspective view showing the components of the cellular system disposed on and within the doll/toy housing of the doll companion system of the present invention.

Advantageously, the NFC interface 78 may enable the CEIL system to engage in near field communication (NFC) with RFID tags, other NFC-enabled electronic devices and other NFC implementations that are currently in place or are being developed for mobile phone integrations. These include, for example, smart poster applications, mobile ticketing, mobile payments and informational NFC tags intended for mobile phones. A growing number of cellular phones are now including NFC readers to interact with these NFC-enabled implementations. For example, posters at some historical parks include NFC tags, museums are placing NFC tags on displays to provide information and Google's Places® implementation is providing local businesses in some cities with NFC tags. Thus, using the NFC reader 15 included in the CEIL system for interacting with the smart cards 86, the child can also make use of other NFC implementations. For example, at a museum or tourist attraction, the child can hold the CEIL reader 15 up to the NFC tag, and information about the exhibit, such as an audio/visual guide, will be displayed on the screen 25 and/or played by speakers 18 (FIG. 18).

Additionally, the technology is already developed for NFC in cell phones, so the technology will be easy and economical to use. Therefore, multiple benefits accrue by using a NFC interface in the smart card system 85.

As shown in FIG. 5, the smart cards 86 are thin cards formed in any of a variety of shapes, made of a child-safe material and made in a size and shape (for example, without sharp corners) suitable for the age of the child. The smart cards 86 are preferably printed with images, numbers, symbols or text to designate particular activities, thereby allowing the child to easily choose the application he wishes to execute. The front and back text and/or images can correspond. For example, the front may show a word in Spanish with the back showing the word in English.

The smart cards 86 may be sold singly or in sets. The applications associated with cards 86 may be any of a variety of types (such as games, videos, animations, pre-recorded audio, media, drawing, coloring, puzzles, mobile applications of online websites such as YouTube® or news sites, music, video clips, learning games, brain teasers, prerecorded lessons, etc.) and may be in any of a variety of categories suitable for children's learning or entertainment. For example, as shown in FIG. 5, the categories may include nature or science cards 86N allowing the child to play science-related games, to view nature videos, etc.; arithmetic cards 86A for teaching math facts; reading readiness cards 86R for teaching sounds, sight words, nursery rhymes, the names of common household items, etc.; foreign language cards 86L that help the child learn a foreign language; sports cards 86S providing instructional videos, team and player stats, etc.; music cards 86M that allow the child to experience a variety of musical styles, sounds, etc.; and movie or video cards 86V that execute the playing of a full-length or abbreviated movie or video.

If the app-initiating smart cards 86 are sold as a set, the cards 86 may be configured with an interior hole 84 for fitting on a ring 82 (FIG. 7) to assist the child in keeping the set together. The ring 82 may be a solid ring with the smart cards non-removable or may have an opening allowing the child to remove the smart cards from the ring and to collect them again onto the ring. Other optional restraining devices may also be used, such as a box to receive and store the cards 86.

Though contactless card technologies are preferred, a contact card technology, such as the familiar magnetic strip technology of passive debit and credit cards can optionally be used by the CEIL system. Magnetic strip cards meet established International Organization for Standardization (ISO) standards defining physical properties of the card, data formats, etc. When using magnetic strip technology, data designating the application to be executed by the CEIL system are embedded in magnetic particles on a band (magnetic strip) attached to the surface of the card. The card reader 15 includes a magnetic reading head and the magnetic strip-type smart card 86 requires physical swiping in the slot of the magnetic strip reader past the magnetic reading head.

The app-initiating smart card system 85 provides a method of self-directed learning and entertainment for the child. Though the parent has the opportunity to schedule educational, entertainment and alert events into the child's daily schedule 745 (FIG. 40), the smart card system 85 allows a specific activity to be chosen by the child. The smart card may be associated by the parent with a particular activity (319, FIG. 37) or the smart card can be pre-assigned to a particular activity.

For example, a collection of bedtime stories can be sold on a CD ROM or DVD with a collection of smart cards 86 (and, optionally, a book of the same bedtime stories). Using the individual-type card of FIG. 7, each card 86 in the set is pre-assigned to correspond to a story in the collection of bedtime stories. As shown in FIG. 37, the bedtime story set is acquired 312 and delivered 315 to the CEIL system. When the child wishes to hear a bedtime story, he selects the card 86 having a picture or graphic that indicates to the child the bedtime story—such as a scene out of the story. The child then taps or waves the smart card 86 in front of the smart card reader 15 (FIG. 1, FIG. 3), which causes the CEIL system to activate the particular bedtime story activity, which may include playing a pre-recorded bedtime story, playing an audio reading of the story while showing an animation on screen 25, executing an interactive game based on the story, playing a video of the story, or the like. If the child wishes to have a second bedtime story activity, he waves a different smart card 86 to execute the second activity.

Figure 7:
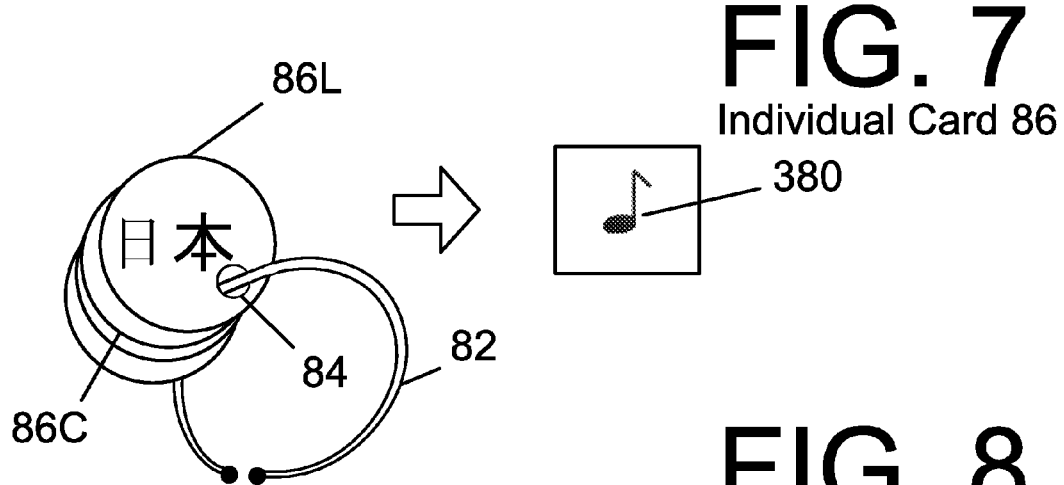
Figure 8:
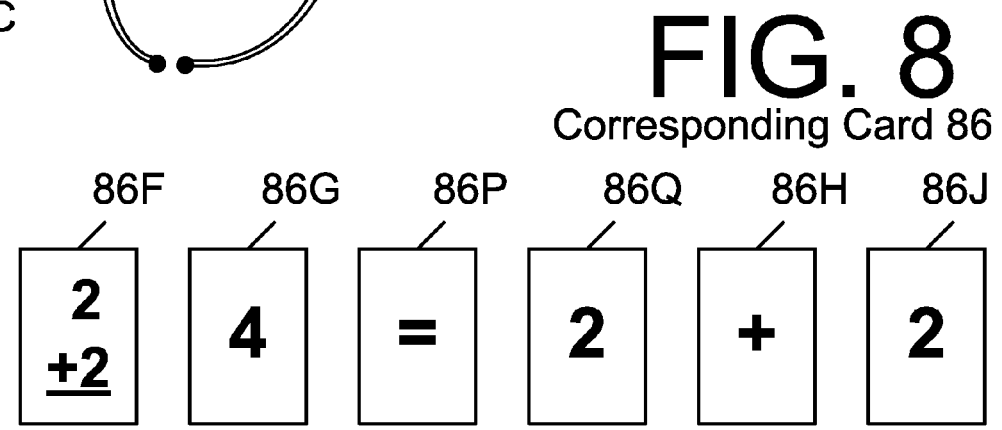

The app-initiating smart card system 85 may be configured to correspond an activity or activities to the smart card 85 in any of a variety of ways, including representative (FIG. 6), individual (FIG. 7) and corresponding (FIG. 8).

Figure 6:
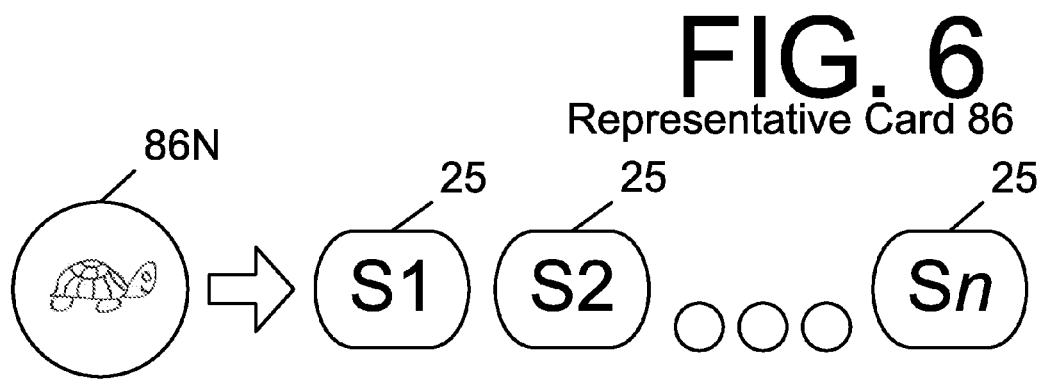
FIG. 6 to FIG. 8 are schematics showing the methods of usage of the smart card system 85 of the doll companion system of the present invention.

In the representative usage of FIG. 6, a single smart card can be representational of a collection of actions, stories or activities. The bedtime story collection described above allows a single smart card to individually execute a single activity (individual usage, FIG. 7). In contrast, as shown in FIG. 6, a single smart card 86N may represent a collection of activities, such as animal videos. When waved by the child in front of the card reader 15, one S1 of the collection of animal videos may be played for the child on screen 25. A second wave of the same card by the child activates the CEIL system to play a second video S2, and so on and so forth up to the number of pre-recorded and installed videos Sn.

In the individual type of usage, shown in FIG. 7, a single card activates a single activity, story, action, etc. For example, when the app-initiating smart card 86L is waved in front of the card reader 15, the CEIL system is activated to play a single Japanese nursery song 380. If a different nursery song is desired, a second smart card 86C associated with the second song would be waved, and so forth.

Turning to FIG. 8, in the corresponding mode of usage, a first card is read by the card reader 15 causing the CEIL system to request a second card having a type of correspondence. For example, if the card 86F (2+2=) is read by the card reader 15, the CEIL system requests the card 86G (4), which is the answer to the math problem and teaches the child the answer to the math fact. Another exemplary use of the corresponding mode allows the child to use the CEIL system as a teaching calculator, as follows: [1.] The child holds a first number 86J in position for reading by the card reader 15. [2.] The child holds a mathematical function symbol 86H in position for reading by the card reader 15. [3.] The child holds a second number 86Q in position for reading by the card reader 15. [4.] The child holds a mathematical function symbol for "equals" 86P in position for reading by the card reader 15. [5.] The CEIL system performs the mathematical operation and announces the answer to the math problem to the child. [6.] If the child holds the number 86G corresponding to the correct answer announced in position for reading by the card reader 15, the CEIL system will play an encouraging message and/or display a short animated video, preferably having an association with the correct number, such as four clowns dancing or the like. The corresponding card may be requested by a pre-recorded message, by a computer-generated verbal message, by an on screen prompt, etc.

Other similar learning and entertainment games can be played using the app-initiating smart card system. For example, a grandparent can record a story that can be associated with a particular smart card 86. The child can then listen to that story by selecting (preferably based on a picture on the particular smart card 86) that particular smart card 86.

Incorporating features of the smart card system 85 with the other systems of the invention may allow additional expansion.

Thus, using the smart card system 85, the child can select the activity of his choice from among the sets of cards 86 available to him.

The smart cards 86 may be acquired 312 (FIG. 37) in any of a number of ways. As discussed later in relation to FIG. 14, the parent may use a computer or the touchscreen 25 to access a web-based interface 103 or an applications store administrative interface 107 to search 310 for, select 311 and download an application (free or with payment). Though the application can be downloaded to the computer and sent to the CEIL system or pushed to the CEIL system using over-the-air technology, obviously a card 86 to initiate the application cannot be downloaded. Thus, the application will be available immediately for use, but the smart card 86 must be obtained through a different means. The corresponding card 86 may be mailed to the purchaser of the application from the application provider. Unassigned cards may be provided at the time of purchase of the CEIL system or may be available through a retailer. The unassigned cards may be printed with various designs (allowing the parent, for example, to choose an unassigned card printed with a kitten image for correspondence with a downloaded pet application) or may be blank and ready to receive a label. After purchasing the application 100 the parent can select an unassigned card at random and associate or correspond 319 a unique number printed on the card with the downloaded application. The unassigned card could further be customized by printing and adhering an image associated with the downloaded application, such as might be provided in association with the downloaded application.

The parent may also purchase pre-assigned smart cards 86 from a retailer, such as a set of cards 86 with zoo animal pictures for playing short zoo animal videos. A media disk, such as a DVD or CD ROM, can be sold with the card 86 set, with the media disk inserted into a computer connected to the CEIL system and the content delivered to the CEIL system. However, if use of a computer is not desired, the child (or parent) can hold a card 86 (such as a lion card) up to the card reader 15. The card reader 15 reads the unique application-associated data and transmits the unique application-associated data to the computer system 40. The computer system 40 compares the newly-received unique application-associated data to the unique identifiers of the installed applications. If the newly-received application-associated data is not found in the unique identifiers of the previously installed applications, the computer system 40 is configured to download the purchased application associated with the newly-received unique application-associated data via the cellular connection (or optionally, via Wi-Fi, if enabled). Optional data may be included on the card to limit the number of downloads of the application (such as to minimize sharing of the card and application between friends).

The smart cards 86 may also be acquired by calling customer service 104, 105 with the application pushed to the CEIL system and the card 86 mailed to the parent or a generic card associated 319 by the parent.

Figure 9:
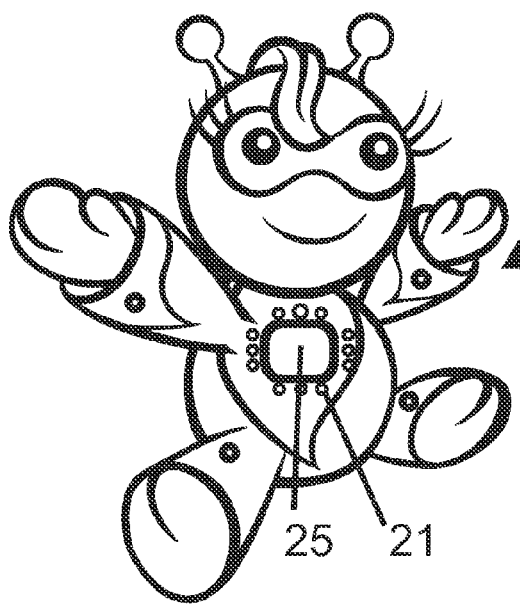
FIG. 9 is a perspective view showing a first exemplary exterior of the doll companion system of the present invention.
Figure 10:
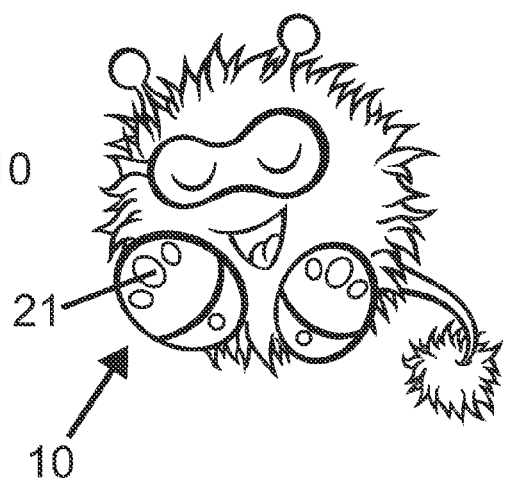
FIG. 10 is a perspective view showing the second exemplary exterior of the doll companion system of the present invention.
Figure 12:
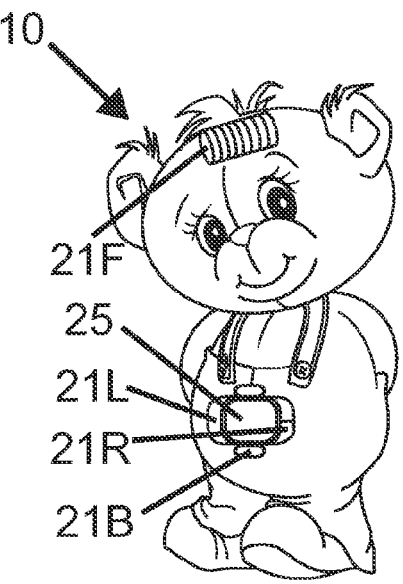
FIG. 12 is a perspective view showing the fourth exemplary exterior of the doll companion system of the present invention.

1.2 Tactile Buttons FIGS. 9-10, 12

Tactile buttons 21 are provided to allow even a very young child a convenient means of input, such as to make a selection, to initiate an application or to interact with a display on screen 25. Moreover, by using tactile buttons 21 in conjunction with the display screen 25, a limited number of tactile buttons 21 are leveraged into an infinite variety of content selection means, since the display screen 25 can be infinitely varied.

In yet a further novel feature, the tactile buttons 21 may be positioned in proximity to the doll companion's display screen 25, such that content displayed on the screen 25 may be associated, even by very young children, with the tactile button 21 in immediate proximity to it. For instance, the system may say "find a red button" while the screen turns red. If the child does not immediately press the red, tactile button 21, the screen 25 may display an arrow pointing at the red button 21 adjacent to the screen to help the child learn colors. The CEIL system may request a button 21 of another color, creating a game for the young child that can be timed to add incentive. In this way, a limited number of physical, tactile buttons 21 may be leveraged—through association with the infinite variety of content that can be generated on the doll companion's display screen—to provide an infinite variety of education and entertainment options that very young children can select by means of the self-direction made possible through physical, tactile buttons.

Looking more closely at the tactile button 21, it is a tactile apparatus allowing the child to touch, feel and manipulate it. The tactile button 21 can be designed to match the age bracket of the child and can be a manually-activated button, a grasping device, turning knob, joystick, pull handle, a rolling bar 21F (FIG. 12), switch or other child-engagable tactile control. The tactile buttons 21 can be tightly integrated with the screen display. The tactile buttons 21 may be colored or may be configured to change colors or to blink to facilitate usage by the installed applications 100. FIG. 12 shows an alternate number and arrangement of tactile buttons 21, with wider top and bottom buttons 21B and wider side buttons 21L, 21R.

The tactile buttons 21 are configured to allow the child to interact with the doll companion, to execute applications (such as by an application-assigned button 21E, FIG. 3), or to activate the cell phone (such as with a speed dial, single-push, "call parent" button 21X). The tactile buttons 21 can be engaged by the child in response to prompts from the display screen 25 or may be configured to consistently perform a particular action, such as the "call parent" function of tactile button 21X.

Figure 11:
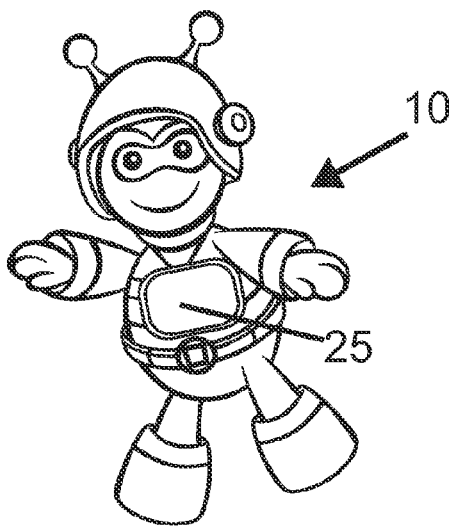
FIG. 11 is a perspective view showing the third exemplary exterior of the doll companion system of the present invention.

The tactile buttons 21 may be separated from the display screen 25 or may be adjacent to the display screen 25. For example, the character of FIG. 9 may be appropriate for the three to five year age group with numerous tactile buttons 21 allowing convenient interaction for the pre-school child. Yet the character of FIG. 11 (without tactile buttons 21, but in which the display screen 25 is a touch screen) may be appropriate for children older than around five years who can easily interact with the touch screen. For these relatively older children, the touch screen 25 may even provide an on-screen dial pad to allow the child to call out to a specific number (with or without inclusion of speed dial button 21X, FIG. 3). The character of FIG. 10 may be appropriate for the youngest infants, who can neither interact with tactile buttons 21 nor efficiently view a display screen 25.

2. Parental Configuration Interface

Though the CEIL system is fully functional as a smart cell phone directly upon purchase, the parent can customize the CEIL system for the particular child's needs and schedule—plus can download new applications and content—through use of any of the multiple configuration interfaces herein provided. The convenient configuration interfaces allow the following: (1.) easy setup, administration and modification of the settings, configurations and protocols of the various systems; (2.) downloading of applications that take advantage of the functions of the systems and expand the programming and content; (3.) establishment and modification of a daily learning, entertainment and alert schedule for the child; (4.) customization of the integrated systems of the doll companion to meet the changing learning needs of the growing child; (5.) configuration with or without physical access to the doll companion; and (6.) configuration with or without Internet access.

Figure 14:
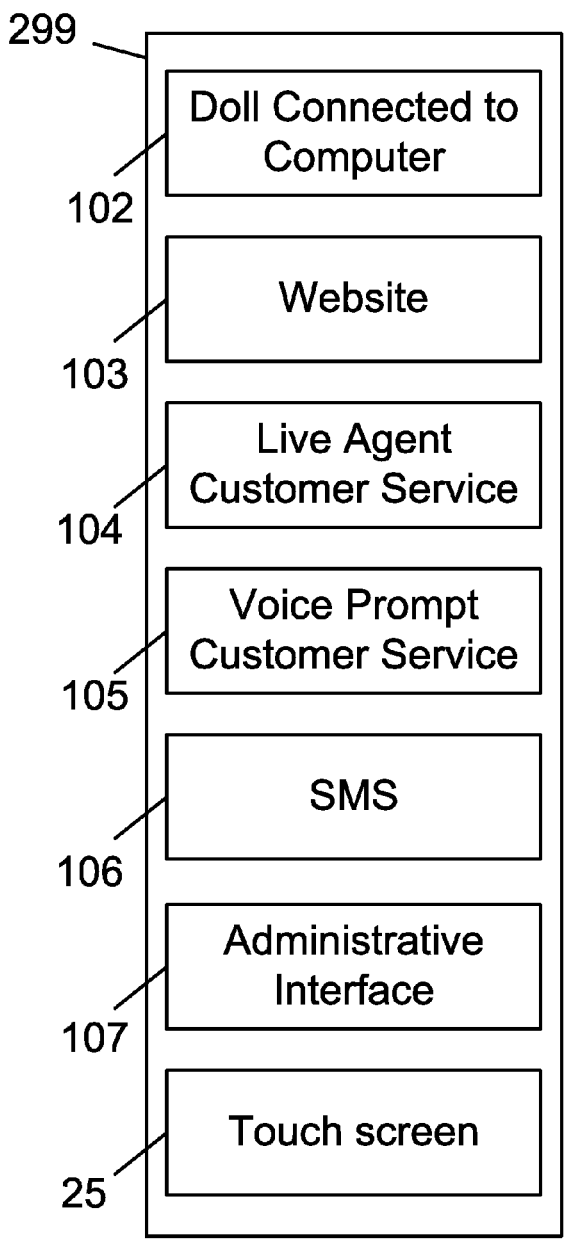
FIG. 14 is a schematic showing parent-access means by which a parent can access the configuration interface to modify configurations and to purchase and download content and applications.

2.1 Parent Access to Configuration Interface—FIG. 14

As shown in FIG. 14, the parent can conveniently access 299 the configuration interface in any of multiple ways. The parent may choose the method of access that is most convenient for him or her. Significantly—and in contrast to prior art smart dolls which are accessed by means of computer technology—the present invention benefits from cell-phone communication. Thus, parents can interact with the doll companion even (a) if they do not use computers or have access to a computer, and (b) even if the doll companion cannot be connected, through wired or wireless means, with a computer, e.g., the doll companion is out of Wi-Fi range.

For example, the parent who lacks facility with computers, or who lacks access to a computer, may access at least a portion of the configuration interface through Short Message Service (SMS) text messaging 106 using coded prompts. For example, a mother on a business trip can text, "alarm=7:30 a.m.," setting the CEIL system alarm to be sure her child is awake in time for school, in case her husband at home forgets to set the child's alarm.

Alternatively, a parent who lacks facility with computers, or who lacks access to a computer may call customer service and reach a live agent 104 who talks the parent through choices provided by the configuration interface. The customer service agent assists the parent in modifying his child's CEIL system or in purchasing applications. For instance, this allows the parent on a camping vacation (who has no access to a home computer or the Internet) to phone the customer service agent and to authorize purchase of new content that is relevant to the local geographic area. The new content is pushed by the cellular provider to the CEIL system, such as by using over-the-air technology. Over-the-air technology allows the remote parent to communicate with, download applications to and manage the CEIL system without being connected physically.

Similarly, when the parent calls the customer service center, instead of, or in combination with, the live agent, the parent may access a voice prompt or automated voice configuration 105 system and initiate downloading of applications or cause modification of the CEIL system within his child's doll companion. For example, if the child has wandered away at a theme park, the parent can call the automated system, choose the correct voice prompt, and trigger the anti-wandering alarm on the child's CEIL system. The loud, unique sound allows the parent to quickly find the child in the crowd.

The parent at home who has facility with computers and who has access to one, and who has ready access to the physical doll companion, may choose to use a computer-based software configuration interface installed on a parent-accessible computer. The parent connects 102 (wired or wirelessly) the CEIL system computer to a user computer having a configuration program installed. After using the configuration interface, the updated settings and/or content are locally transferred to the CEIL computer through a local communication method. The local communication method may include Bluetooth® transmission, a home wireless network connection, a physical connection (such as by connecting a USB cord between the CEIL computer via doll connection 77, FIG. 18, and the user computer), or other standard local networking methods. For example, the parent purchases the doll, installs the configuration interface software on the home computer, connects the doll and personalizes the child's daily schedule of learning, alert and entertainment activities.

Where the doll companion is not in close physical proximity to a computer, configuration and application downloading may be done remotely using a web-based interface 103 with remote updating of the configuration settings and installation of the downloaded applications of the doll companion enabled through the cell provider's "push" functionality via the cellular network. This feature takes advantage of the ubiquity of cell service, so that applications may be downloaded to the doll companion, virtually, wherever it is. Of course, if Wi-Fi is available, this may optionally be used to download applications to the doll companion via the Internet. For example, using this web-based push system, the parent at work logs onto (such as by user name and password) the web-based interface, purchases a new learning game application or new video content; the application or content is pushed to the child's CEIL system at home.

The administrative interface (FIG. 16) provides management of applications and connectivity to an applications store for downloading of applications. The administrative interface may be provided through an installed application on a computer, a web-based service, or an application on the parent's cell phone.

The touchscreen 25 of the CEIL system can also provide access to the configuration system. For example, from the campsite, using cellular phone connectivity (such as 3G or 4G) the parent can use the touchscreen 25 to purchase and download a new game to occupy the child while driving home from the camping trip.

Thus, the parent can use any method of accessing the configuration interface that is most convenient at the moment, including methods dispensing with the need to use a computer, and including the capability of interacting with the doll companion when it is out of wired or Wi-Fi range. Through the use of one of the access methods, the parent in any of a wide variety of situations can modify the settings of the CEIL system, change the child's schedule and buy applications and content that is delivered seamlessly to the child's CEIL system.

Figure 15:
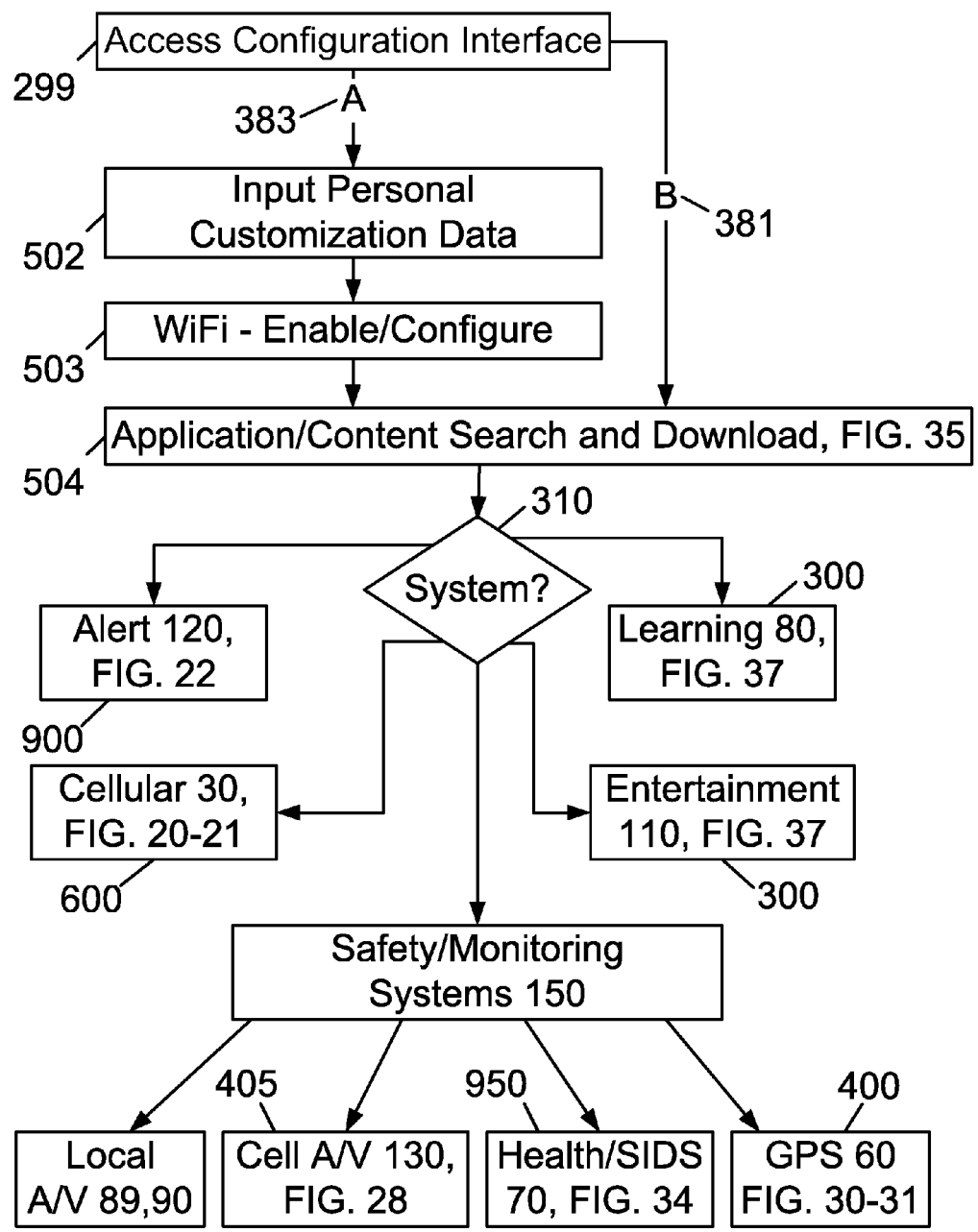
FIG. 15 is a schematic showing an overview of an exemplary configuration interface used to search, purchase and download applications, and used to initialize, configure, reconfigure and update the various systems of the doll companion system of the present invention.

2.2 Configuration Interface Overview—FIG. 15

The initial configuration of the CEIL system at the time of purchase provides smart cell phone functionality; however the initial functionality (cell phone and other systems) is based on preset options and settings. Therefore, to utilize the full functionality of the CEIL system, a configuration interface is provided. The general configuration interface is shown in FIG. 15, with the configuration of particular systems shown in later figures.

The configuration interface allows the parent to select and optimize functionality including enabling, disabling and customizing systems. The configuration interface offers selections based on age, ability and interest of the child. Using the configuration interface the parent can initialize, upgrade, reset or reconfigure the CEIL system, plus the parent can download and purchase applications and new content. The configuration interface is available to reconfigure functions and applications as may be needed when the needs of the child change, upon adding new applications or hardware, after a software update, after a hard reset of the system or other similar events.

As shown in FIG. 15, the parent accesses 299 the configuration interface using any of the methods discussed in relation to FIG. 14.

FIG. 15 shows both an initialization Pathway A 383, used in the initial setup of the CEIL system, and a reconfiguration Pathway B 381, used to download new content or reconfigure one of the subsystems.

In the initial setup, pathway A, the configuration interface requests personal customization data, which is input 502 by the parent. The requested customization data allow the software and applications to personalize the communication and interaction between the doll companion and the child. Requested customization data include a request of the name of the child (for example, "Rylee") and the names with which the parents or other adults wish to be referred (for example, "Mommy" and "Papa"). Preferably, the customization data request further personal details to be utilized in the functions of the CEIL system. These further customization data may include the names with which the grandparents or other relatives wish to be referred, pictures of relatives, the street address and state of the child, the age of the child, names and ages of brothers and sisters of the child, names of the child's friends, the child's favorite food and color, the birthday of the child, etc.

After initial requested customization data are input 502 by the parent, the parent may be offered the choice of enabling and configuring 503 a local Internet network or Wi-Fi, which is typical with conventional smart phone setup. This allows the CEIL system to take advantage of a broadband network connection, such as a home or school network, to minimize usage of the cell phone minutes or data plan. Additionally, the parent is offered the opportunity to search for and download 850 applications and new content, described in association with FIG. 16.

Figure 34:
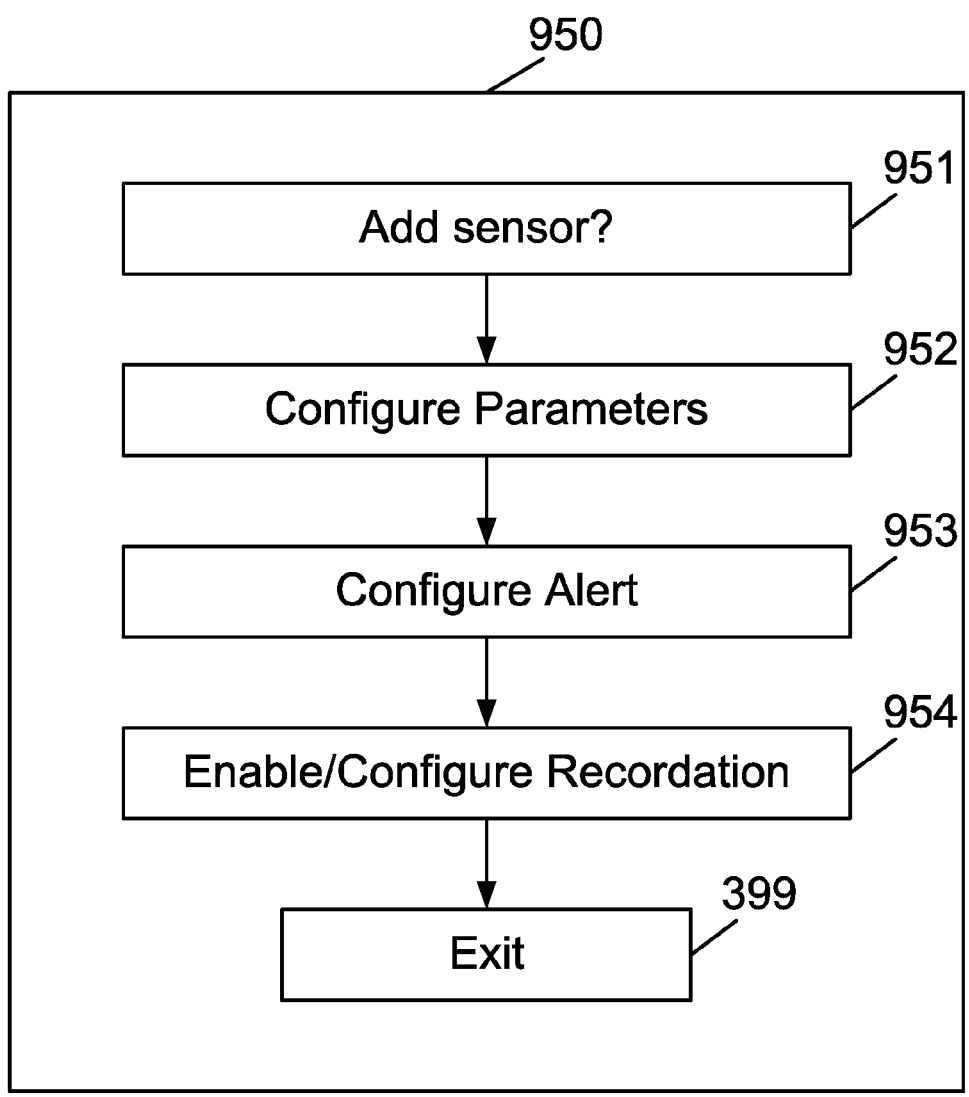
FIG. 34 is a schematic showing an exemplary configuration interface for configuring the health/SIDS monitoring system.

The parent is then offered the opportunity to select 310 one or more of the systems to initialize, reconfigure or change. These systems include the cellular system configuration interface 600 (FIGS. 20-21), the learning and entertainment configuration interfaces 300 (FIG. 37) and the monitoring configuration interfaces including cellular audio/video monitoring 130 interface 405 (FIG. 28), GPS monitoring system 60 interface 400 (FIGS. 30-31) and health/SIDS monitoring system 70 interface 950 (FIG. 34).

Generally, the cellular system 30 will be enabled and configured first, as many functions require this system. However, in particular instances, a focus may be placed on one or more functions of the CEIL system that do not require the cellular system. For example, the CEIL system might be provided to a child during an extended hospital stay merely for the comfort provided and for the education system 80 and entertainment system 110, without using the cell phone connectivity. Thus the CEIL system can be configured to provide limited functionality without the cellular system 30. If configured for temporary use without the cellular system 30, the cellular system 30 can be enabled later, for example, when the child leaves the hospital to go home.

Figure 16:
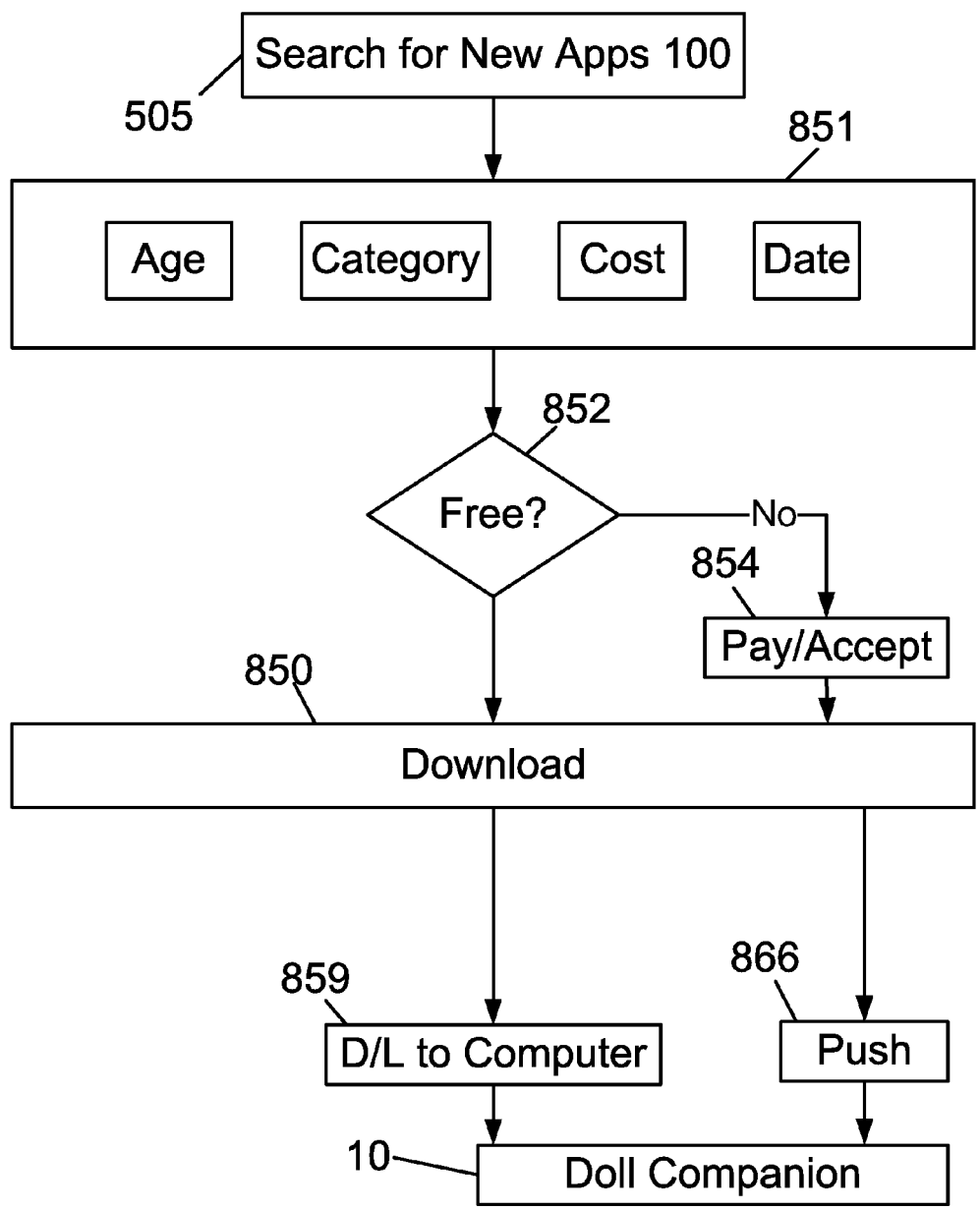
FIG. 16 is a schematic showing a portion of the configuration interface for obtaining new applications (including both executable applications and content) to be installed into the doll companion system of the present invention.

2.3 Parent Download and Install Applications—FIG. 16

Though the CEIL system is preloaded with software providing some functions, the system is designed to allow and encourage software developers to create applications 100 that utilize the elements and functionality of the system. Through the selection, downloading and installation of new applications, the CEIL system will continue to challenge, educate and entertain the child.

A convenient administrative interface allowing search and downloading of applications is provided. This administrative interface provides connectivity to an applications store, such as the iTunes® App Store® or the like. The administrative interface may allow selection and download not only of applications 100, but also of content such as images, videos, ringtones, audio books, media and the like. The administrative interface preferably provides a means to purchase applications 100 that are offered for purchase.

The parent is able to search 505 for new applications 100. Various filters 851 can be applied to assist in finding a desirable application 100. If the application is free 852, the application can be immediately downloaded 850. If the application is not free 852, payment 854 can be made before download 850. The application can be pushed 866 to the CEIL system or downloaded 859 to a computer that is connectable to the CEIL system for transfer of the application.

Thus, by using the administrative interface, the parent can change the CEIL system based on the child's needs and changing schedule. Learning applications 100 may be downloaded based on the learning progress and current interest of the child. Some applications 100 may call for an enabled Wi-Fi connection (503, FIG. 15) either for full functionality or to minimize cell phone charges, such as for Skype® video conferencing.

The media download user interface may also be functional to manage the contents on the CEIL system.

Figure 17:
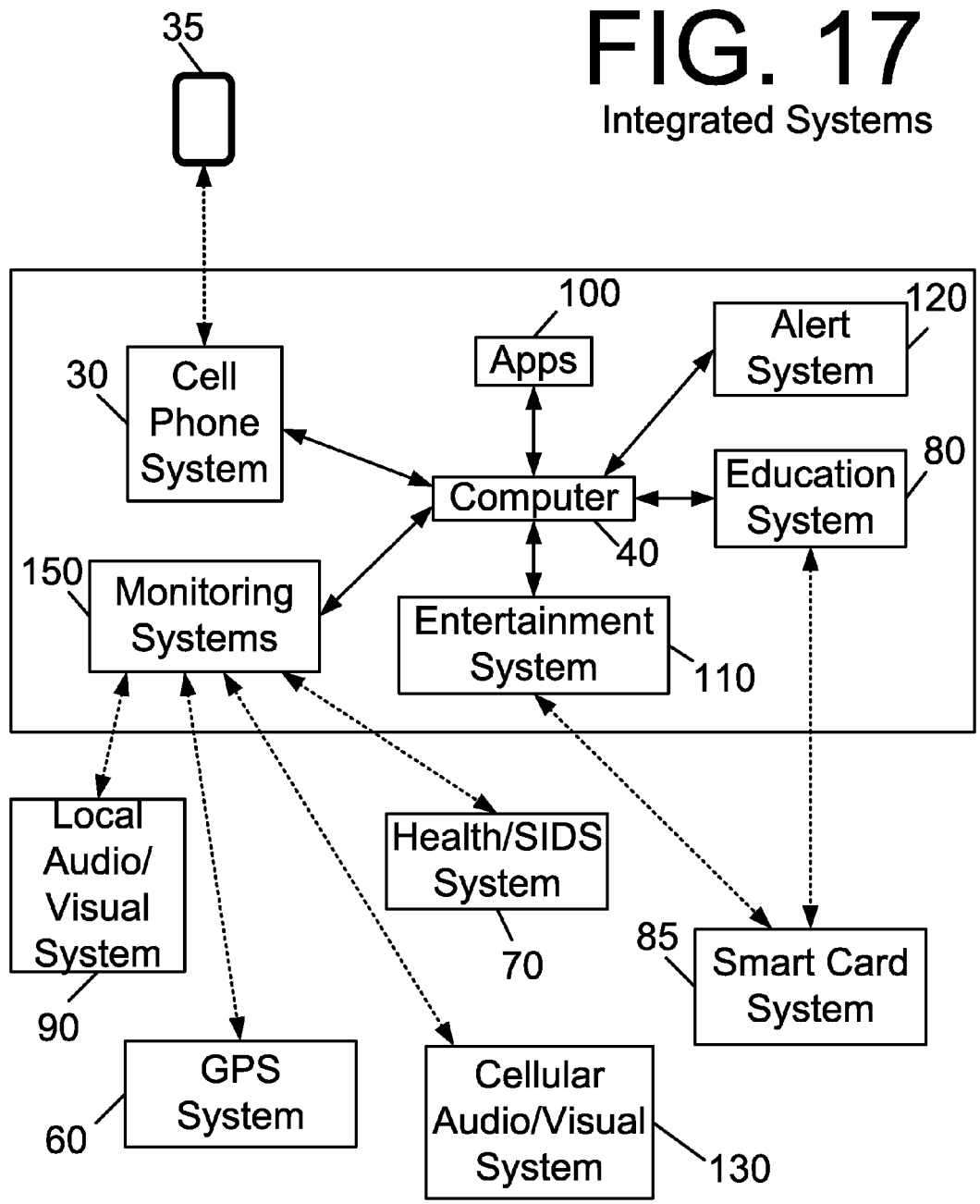
FIG. 17 is a schematic showing an overview of selected aspects of the integrated systems of the doll companion of the present invention, including the cell phone communication, education, entertainment, alert and monitoring systems.

3. CEIL System Integration Overview—FIG. 17

The CEIL system not only uses the ubiquitous in-place cellular service infrastructure to provide efficient cellular communication 30, it also layers safety and security monitoring 150, educational instruction 80, alerts 120, and entertainment 110 onto the cellular structure, and does so in connection with novel means enabling even very young children to interact with the system.

In the CEIL system the capabilities and functions of the cell phone system 30 are combined in various ways with the other systems, with variations in the methods that the child can control the CEIL system, and with the ability of the parent to configure the CEIL system to meet the specific needs of a child (from birth to around 8 to 10 years of age). The versatility of the system combinations allows age-appropriate and ability-appropriate interaction between the child and the doll companion, while allowing a parent to monitor and communicate with the child. Additionally, the system capabilities and functions plus the child control of the system (child-activated input devices 45, FIG. 13) are accessible for use by independently developed applications 100, such as may be purchased and downloaded from an applications store or market. The CEIL system can change and adapt as the child grows. For example, the CEIL system may be purchased for a newborn for the SIDS and surveillance monitoring functions. But the CEIL system will not become obsolete when the danger of SIDS is diminished at the age of one year, due to the cell phone capability combined with the parent's ability to customize the CEIL's child schedule and the availability of the variety of applications 100 for the toddler, preschooler and elementary child. Therefore, the child will not quickly outgrow or become tired of the CEIL system—it can be updated with new applications to challenge and engage the child as he grows and his interests change.

A single doll companion of the CEIL system encompasses the benefits of multiple learning toys, electronic toys, educational computer programs, entertainment devices and monitoring or alert mechanisms, while adding new functionality. Thus the life of the parent and child is simplified, portability is increased, and the time and effort involved in charging, maintaining, locating and learning to use the many limited individual electronic devices and toys is reduced.

Figure 13:
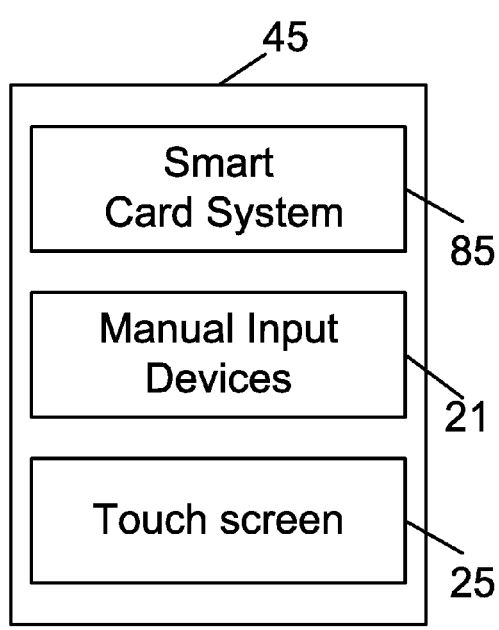
FIG. 13 is a schematic showing child-input means by which a child can execute applications and interact with the doll companion of the present invention.

The CEIL system allows even the young child to select and to execute educational and entertainment applications. As shown in FIG. 13, through use of the child-activated input devices 45 (smart card system 85, tactile buttons 21, the touch screen 25) the child can conveniently self-direct learning and entertainment.

Security is a major concern in our daily lives, especially when it comes to the safety of one's child. More than ever parents are concerned about with whom they leave their child, the character of the school teacher, and the precautions others may, or may not, take in keeping the child safe at all times. The doll companion system brings desired peace of mind to a parent whether the child is in the next room or halfway across the world. The parent on a business trip to California can effortlessly monitor her child sleeping in New York, with only her cell phone required.

Figure 29:
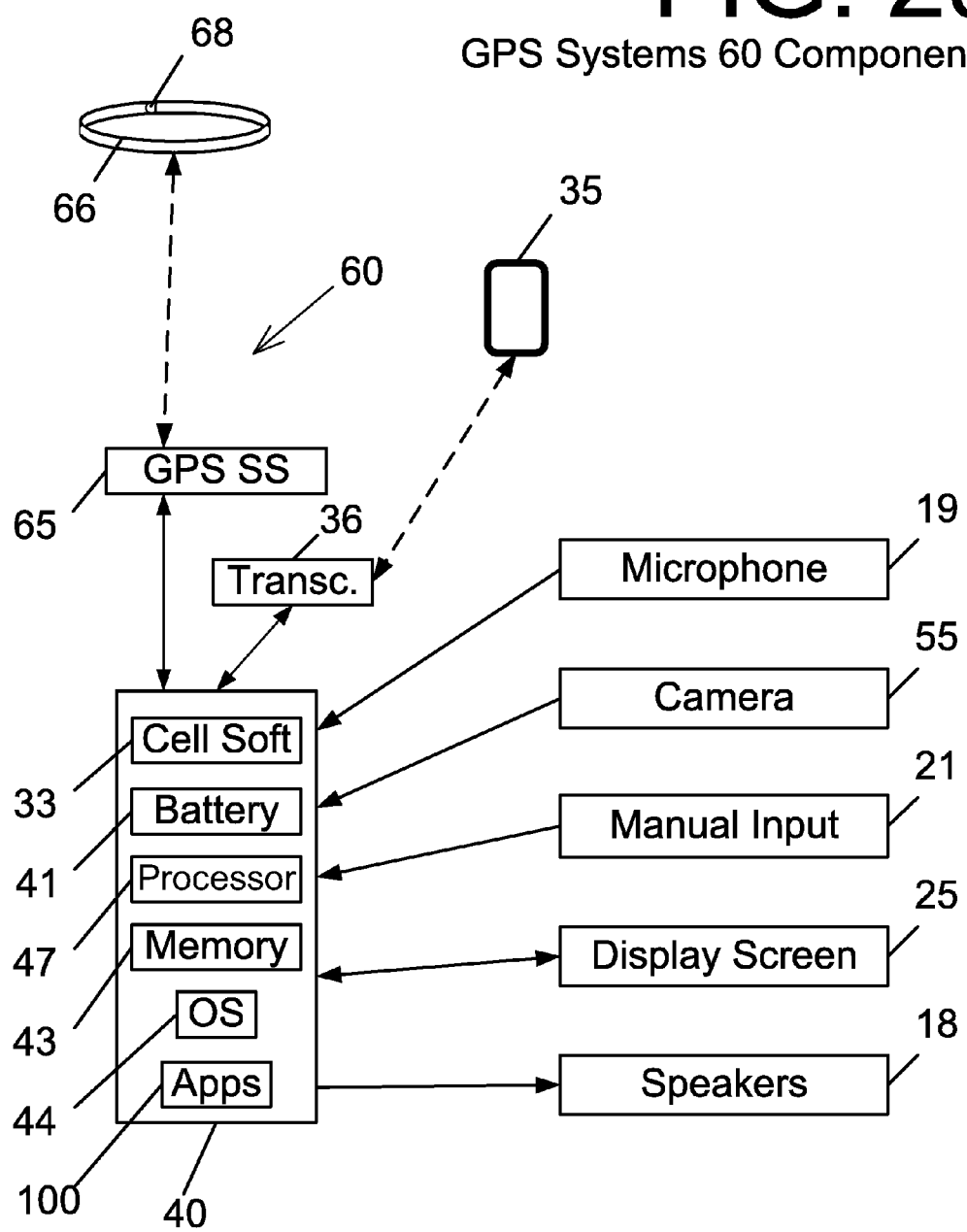
FIG. 29 is a schematic showing the organization of components of the GPS system of the doll companion system of the present invention.

The monitoring systems 150 include the local audio/video monitoring system 90 (including 90A, 90B) the GPS system 60, cellular audio/visual monitoring system 130 and the health/SIDS system 70. The cellular audio/video monitoring system 130 (FIG. 27) allows a parent to receive a live audio and/or video feed from area of the doll companion via a cell phone 35. The local audio/video monitoring system 90 (FIGS. 25, 26) allows a parent to receive a live audio and/or video feed from the area of the doll companion via a receiver 56, 57. The GPS monitoring system 60 (FIG. 29) works along with a wearable paired device to provide location-based information. The health/Sudden Infant Death Syndrome (SIDS) system 70 (FIG. 34) uses sensors to detect that the baby is moving and breathing or to monitor health issues of the child. In one aspect, the CEIL system employs NFC for reading the GPS safety band and/or the SIDS/health monitor, as well as the smart card.

Another concern of parents is the education of the child. The doll companion system allows both parent-directed (daily event schedule, FIG. 40) and self-directed learning (FIG. 13). The learning 80 and entertainment 110 systems can be changed and updated to meet the ever-changing needs of the child.

The education 80 and entertainment 110 systems (FIGS. 35-37) provide an assortment of entertainment and learning opportunities for the child. The configuration interface (FIG. 37) provides a method to change, update and adjust the content according to the child's needs and abilities. The doll companion grows with the child by enabling the loading of new digital content and new applications 100 and by changing the child's schedule (FIGS. 38-40). The app-initiating smart card system 85 (FIGS. 1-7) allows the child to execute education 80 and entertainment 110 applications at will.

Figure 22:
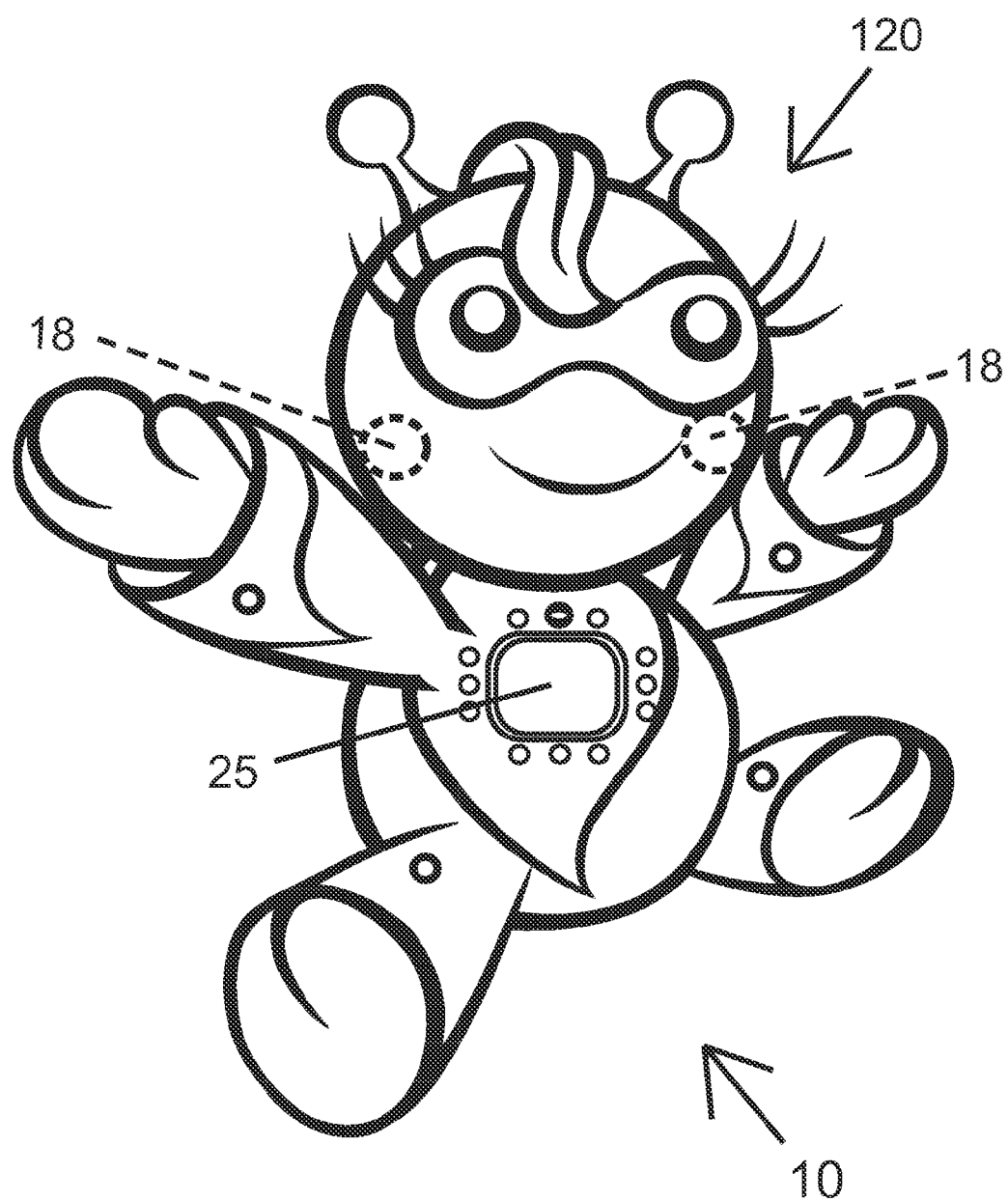
FIG. 22 is a perspective view showing the components of the alert system disposed on and within the doll/toy housing of the doll companion system of the present invention.

The alert system 120 (FIGS. 22-23) enables the parent to set alarms, notifications, helpful reminders and other alerts for the child.

Also included is a computer system 40 operable to execute the variety of programs and applications 100 needed to implement the functionality of the other systems and subsystems. The computer system 40 also enables and operates components of the CEIL system, including input and output devices.

The versatility and configurability of the doll companion system allow it to efficiently meet the needs of children of different ages. For example, the doll companion system may include different elements and functions when designed for infants, preschoolers or elementary children, though overlap in usage of some aspects of the multiple systems occurs between age groups.

4. Exterior Appearance Overview—FIG. 9 to FIG. 12

The doll/toy housing of the doll companion may have any of a variety of exterior appearances designed to appeal to boys or girls of differing ages. A small selection of the many possible exterior appearances of the doll/toy housings are shown in FIG. 9 to FIG. 12. For younger ages the doll/toy housing may lend itself toward a doll configuration, for older ages the doll/toy housing may assume a toy-like exterior. To draw and keep the child's interest, the exterior appearance may be associated with a particular character, with each different character having a unique personality and background story line. The exterior appearance of the doll companion 10 may manifest the personality.

For the younger age groups, the doll/toy housing is preferably formed of a soft, child-safe exterior; the exterior may be plush, may be a soft smooth synthetic material, or may be a combination of materials suitable for a child. Other doll/toy housing exteriors may be appropriate for other ages. For example, a girl's doll companion may be pink and sparkly. Or the doll companion may be embodied in a transforming mechanized toy to appeal to boys in the older age group. Or the CEIL system may be sold as a modular component of a kit suitable for integrating with a "build your own" exterior, such as built with Lego® brand structural building blocks. Portions of the doll/toy housing may be covered with clothing, with the restriction that some components need to be accessible to the child so remain uncovered by clothing. Optionally, the doll/toy housing may appear to have clothing with the external surface colored and/or textured to symbolize clothing.

An interior cavity is provided; it is sized and configured to receive and hold the internal components of the CEIL system. The interior cavity may be located in any area of the doll companion 10 of sufficient size. For example, the internal components may be held within the stomach area of the character of FIG. 9, but within the head/body area of the second embodiment of FIG. 10. Preferably, the interior cavity is water resistant or waterproof for durability and protection of the electronic internal components. Preferably, a child-proof securing device 58 (FIG. 18) secures the internal components within the interior cavity of the cell-enabled doll companion.

Some peripheral components, such as input/output devices, though directly or wirelessly connected to the interior components, may be located in the extremities (for example, vibrators 17 in antennas 99, microphone 19 in face, etc.) and/or may be at least partially exposed (for example, camera 55 in eye 91).

5. Cellular Communication System Components—FIG. 18-19

The parent (or grandparent) can view the child and talk to the child through the cellular communication system, responding verbally to both voice messages and gestures viewed through the doll companion's camera 55 and heard through the microphone 19.

The cell phone system 30 is configured as an operational cellular communication system allowing connection to a cellular phone provider; though particular components and functions are called out as they relate to the CEIL system, the cell phone system 30 is not limited to the mentioned components and functions but includes the standard components and functions of a smart cellular phone, as is well known in the art. The CEIL system includes standard cellular transmitting and receiving hardware, referred to as transceiver 36. The cellular system 30 may use voice communication channels and/or data communication channels.

As shown in FIG. 18, the cell phone system 30 may utilize multiple ones of the following input/output devices: display screen 25, tactile button 21, 21X, speaker(s) 18, camera 55, microphone 19, lighted elements 14 and vibration mechanism 17.

In the exemplary character shown in FIG. 18, the display screen 25 is an interactive touch screen embedded within the stomach area 93 with tactile buttons 21 disposed around the touch screen and on the doll companion's extremities. The tactile buttons 21 are configured as operable input mechanisms allowing the child to touch the tactile button 21 to control or interact with the CEIL system. At least one tactile button 21X is configured as a one-touch speed dial.

Figure 19:
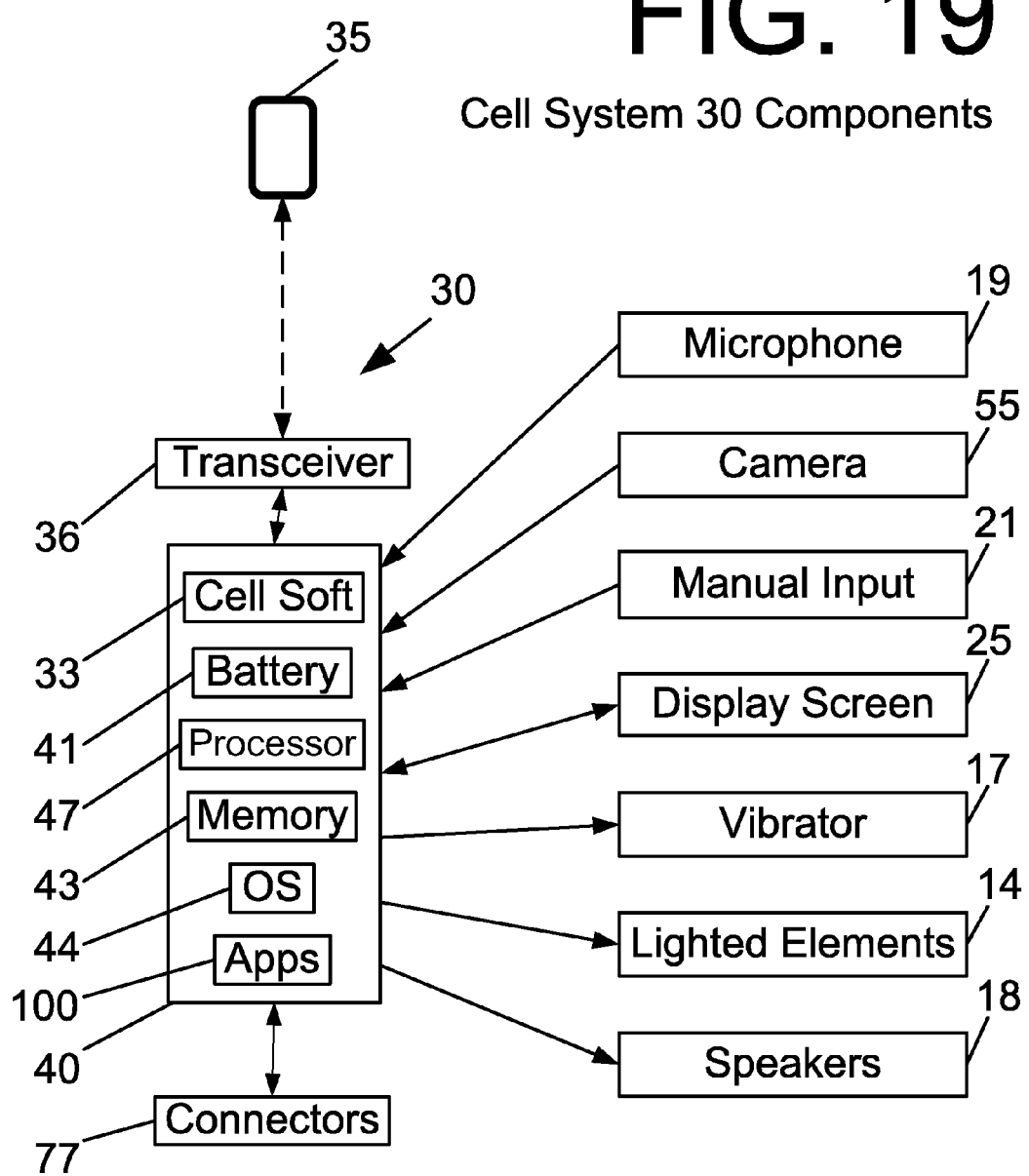
FIG. 19 is a schematic showing the components of the cellular system of the doll companion system of the present invention.

An operable camera 55 may include a single forward-looking camera (as shown disposed within one of the eyes 91, but may alternatively be disposed in other forward-looking positions) or may optionally include two cameras including a forward-facing camera and a rear-facing camera for optimum viewing of the child's surroundings. The camera 55 is functional to at least record still photographs and, preferably, to record video images. As shown in FIG. 19, the camera 55 is operably connected to the computer system 40 (FIG. 19), which may store the images in memory 43 or immediately transmit the images to the parent's cell phone 35.

One or multiple connectors 77 are preferably disposed in a connection compartment in an obscure and less important area with the shape and structure of the doll companion dictating the location of the inconspicuous space, such as the back or bottom of the cell-enabled doll companion. They are preferably embedded in a manner that allows access for the parent, yet reduces or denies access to the child. Though in some configurations the connectors 77 may be exposed, they are preferably hidden with a covering, child-proof securing device 58. Optionally, child-proof securing device 58 may also provide access to other internal components within the interior cavity of the cell-enabled doll companion for maintenance or repair.

Such a child-proof securing device 58 may be a plate retained by screws, a hinged door with connectors operatable by an adult, or other similar concealing, protective closure as is known in the art. The child-proof securing device 58 restricts child access to the connection compartment, but allows adult access to the connectors 77, battery 41 and other internal components.

Preferably, the child-proof securing device 58 is integrated with the external surface of the doll/toy housing so as to be visually pleasing. For example, a doll companion covered with a plush fabric may have a plush fabric cover adhered by complementary hook and loop closure mechanisms to conceal a plastic plate attachable by screws that forms a door to enclose an opening into the interior cavity.

The standard connectors 77 may include a toy-to-computer connector (allowing the parent to connect the doll companion to a computer to update the software, such as a USB connector) and a power connector (allowing the parent to connect a charger to charge the internal battery 41). Optionally, the connectors 77 can include other standard connectors for connecting standard electronic equipment, for example, a High-Definition Multimedia Interface (HDMI) connector (for transmitting digital data to a digital video player, personal computer, computer monitor, video projector, digital television, etc.), a connection for a removable memory unit, a VGI connector or the like.

Preferably, the components of the integrated systems are generally modular for ease in assembly, removal and replacement for upgrading or maintenance. Preferably, system-to-output device connectors and system-to-system connectors allow easy assembly and removal of the components. For example, a system-to-output device connector (not shown) may be used between the computing system 40 and the speakers 18, thus allowing quick extraction and replacement of speakers 18 or easy disconnection from the computing system 40 when required. Or, the GPS system may be connected to the computer system 40 by a system-to-system connector to allow the GPS system to be easily removed for repair. These modular connectors may be proprietary or may utilize conventionally available types of connectors.

5.1 Computing System, Input and Output Devices—FIG. 19

As shown in FIG. 19, the computing system 40 includes at least one processor with an operating system (OS) 44 implementing the cellular system 30 functionality, accepting installation of processor-executable application instructions 100, allowing execution of processor-executable application instructions 100, and managing the software and hardware resources. The OS 44 may provide (natively or through an installed application 100) a user interface for the child (and, optionally, a parent configuration interface). The hardware and software of the computing system 40 include at least one processor-readable storage medium (memory 43); at least one set of processor-executable cellular system software instructions 33; at least one processor 47 adapted to execute the application 100 instructions, the cellular system software instructions 33 and the operating system instructions of OS 44; an internal battery 41; and multiple input/output devices.

Internal battery 41 may be a conventionally available battery (or set of batteries), chosen based on considerations of durability, capacity, discharge time, current, economics and the like. Due to environmental considerations, the internal battery 41 is preferably rechargeable, though single use batteries could be utilized. Optionally, the internal battery 41 may be easily accessible and replaceable; this allows the parent to keep a second battery (or second set of batteries) charging for replacement on a scheduled basis, to assure that the CEIL system is always functional. An optional low-battery alert system is operable to detect a low battery and to cause the computing system 40 to send an alert to the parent via the cellular system 30 (such as by a pre-recorded message or by text).

The charging device for the CEIL system is operatively attachable to household electrical current. The charging device may be a standard transformer-type corded charger, but preferably may be a charging saddle. The charging saddle is a stand or holder that receives the doll companion and charges the battery of the CEIL system, charging, for example, at times of lower utilization of the doll companion, such as at nighttime. Preferably, the charging saddle uses inductive charging for convenience (the doll companion is merely set upon the charger without the need for a direct, wired contact) and for safety (the battery contacts are completely sealed, preventing touching and exposure to wetness). However, optionally, wired contact may be used between the doll companion and the charging saddle with the transformer connected to a connector (77, FIG. 18).

The charging saddle may be placed in a location that allows the doll companion supported upon or within it to be positioned to allow advantageous views from the camera—while permitting the CEIL system to charge. For example, with a baby, the charging saddle may be a crib mount, positioned near the baby's crib, supported from the crib rail, or placed at the far end of the crib. The doll companion is placed on the charging saddle and supported in a manner that charges the battery while holding the camera 55 in position to allow remote viewing of the baby in the crib.

The cellular system software instructions 33 are configured to provide the functionality of cellular phone service, including allowing the parent to dial into the CEIL system to monitor or communicate with the child, providing the option to allow the child to dial out to the parent or others, and other similar cell phone functions. To allow quick implementation of the current invention, the processor-executable cellular system software instructions 33 of the CEIL system are preferably based on a standard existing cellular phone operating system, though a custom cellular phone operating system can optionally be developed and utilized. The processor(s) 47 is adapted to execute the cellular system software instructions 33. The configuration of the cellular system 30 is described in FIGS. 20-21.

Additionally, computing system 40 preferably provides an application program interface (API), a convenient interface for software developers to access and use the resources of the CEIL system. This allows new useful applications 100 to be developed to utilize the functions of the CEIL system, and to expand education and entertainment content. These newly developed applications 100 are preferably available for download from an applications store.

The display screen 25 is preferably included in the CEIL system for all age groups, although it may optionally be omitted for the youngest ages or for special implementations of the CEIL system. For very young children, the display screen 25 may merely display content, while for older children the display screen 25 may be a fully functional touch screen. The touch screen is operative to display an image and to allow direct interaction through physical contact with what is displayed. The touch screen is operative to recognize the location of the contact, with the response generated by the software running on the CEIL system. Any of the various types of touch screens as are known, or become known, in the art are usable with the CEIL system. These include touch screens that use any of the currently available touch screen technologies, such as resistive, capacitive, surface acoustic wave, infrared, acoustic pulse recognition, optical imaging, dispersive signal, multi-touch and the like.

A microphone 19 is embedded in an area allowing reception of the sounds from the child and the child's environment, such as in the head 22 (FIG. 18) area. The microphone 19 is operably connected to the computer system 40 (FIG. 19). Microphone 19 is operable to record audio sounds and transmit them to the computer system 40.

The two speakers 18 are preferably disposed within the doll companion, such as in the head 22. They are operably connected to the computer system 40 and are configured to output audio data. Speakers 18 are operable for usage by the computer system 40 in implementing installed applications 100. A volume adjustment can be provided locally on the doll/toy housing, within the connection compartment secured by child-proof securing device 58 (FIG. 18), or accessible through the configuration interface. Optionally, a single speaker 18 can be used.

A vibration mechanism 17 is preferably disposed within each of the two antennas 99. The vibration mechanism 17 is a mechanical vibrator that causes the antenna to move or vibrate to create interest. Optionally, lighted elements 14 can also be positioned within or on antennas 99 to create a lighted effect. Lighted elements 14 and vibration mechanisms 17 are operably connected to and controlled by the computer system 40 (FIG. 19). The lighted elements and the vibration of the antenna may be utilized by the cellular system 30 and/or by the applications 100 to cause the doll companion to show excitement, to draw attention, or in other creative ways. For example, the lighted elements 14 can be configured to light up with a red glow when Dad calls with the vibration mechanisms 17 vibrating the antennas 99 to create excitement.

The cell phone system 30 includes an auto-answer feature and, in most embodiments, a one button speed dial 21X (FIG. 18) feature. The CEIL system is programmed during initial setup with the parent's phone number or numbers, both to allow incoming phone calls from the parent and, if enabled, to allow speed dial to a parent. When the parent dials the phone number of the CEIL system, the system recognizes the number and automatically answers the call without ringing or notifying the child. The parent has the option of dialing a specified cue number (such as, for example *133, *888 or the like) that triggers the cell phone system to announce the parent's call. For example, with a young child the announcement might be "Mommy is calling", while for an older child the announcement may be a ringtone.

Various configuration options of the cellular communication system are provided to the parent through the configuration interface.

Figure 20:
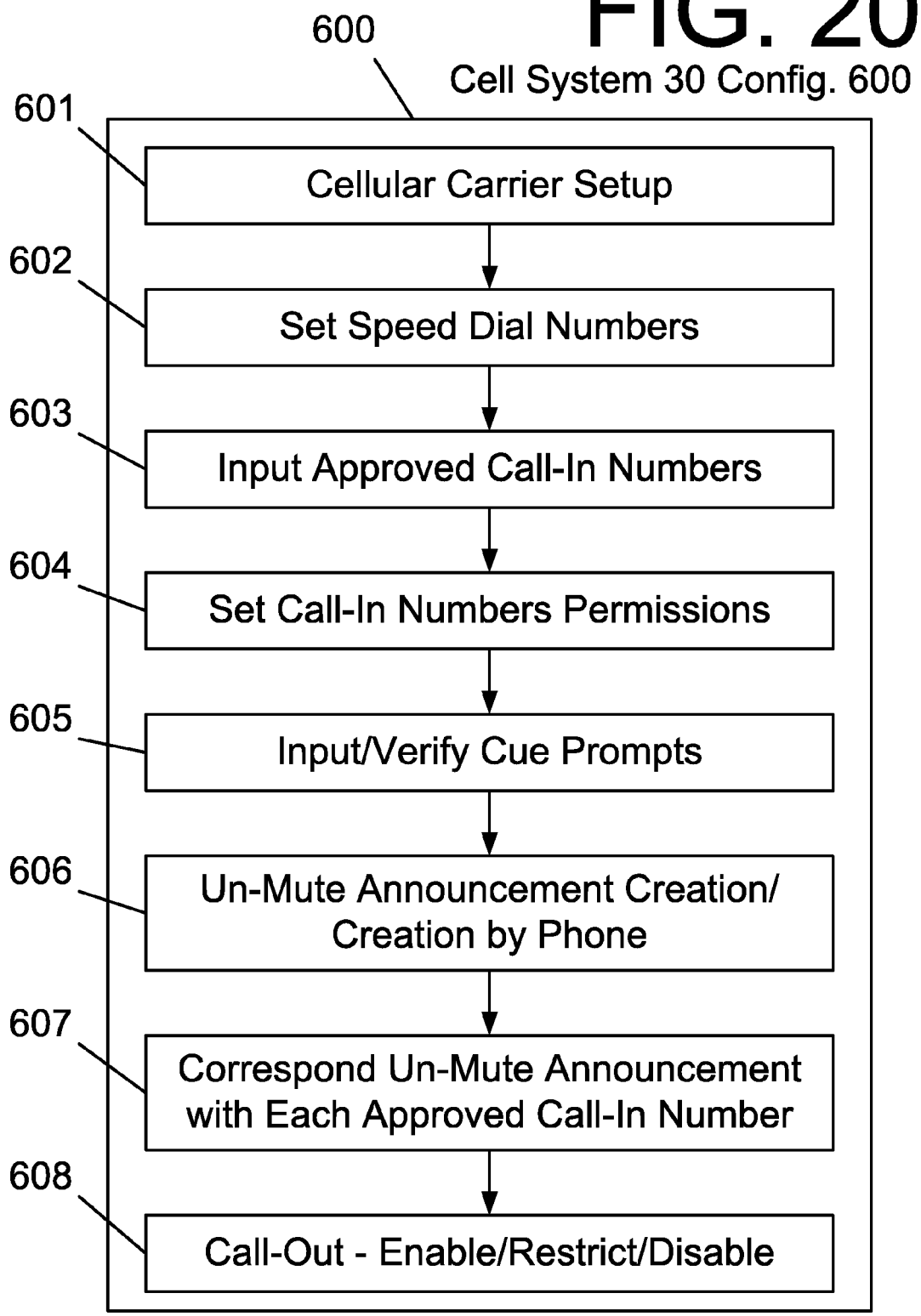
FIG. 20 is a schematic showing an exemplary configuration interface for configuring the cell phone system of the doll companion system of the present invention.
Figure 21:
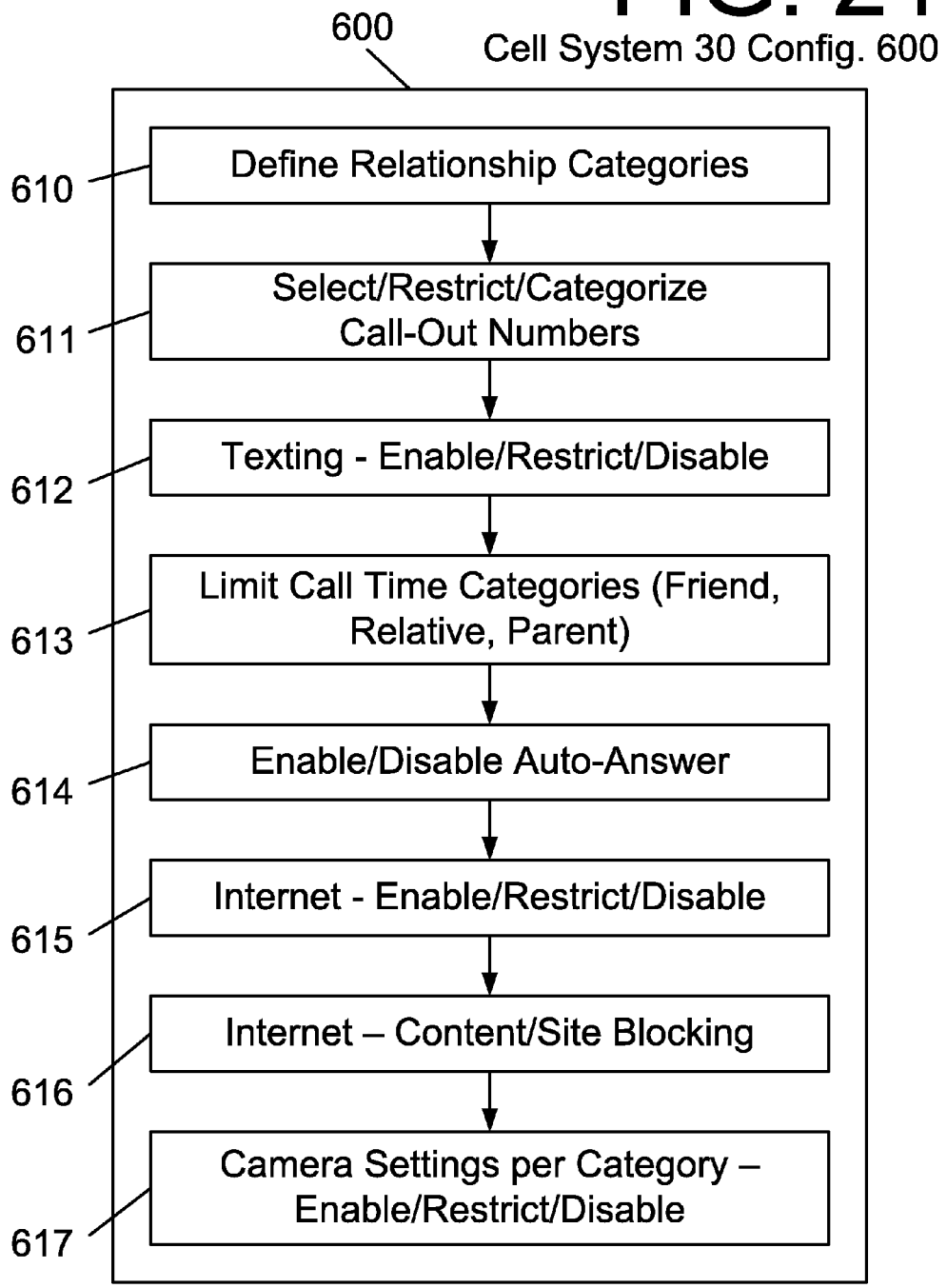
FIG. 21 is a schematic showing an exemplary configuration interface for configuring the cell phone system of the doll companion system of the present invention, particularly for an older child.

5.2 Configuration of Cellular System—FIGS. 20-21

The cellular configuration interface 600 allows configuration of various aspects of the cellular system 30, as shown in FIGS. 20-21. The cellular carrier setup process 601 may include any of a variety of typical cell phone service initiation processes, such as setting up an account with the cellular provider, providing payment arrangements, installing a SIM card, activating the cellular service and the like, the details of which may vary among cellular carriers.

The parent user can set 602 one or more speed dial numbers, allowing the child to touch a single speed dial button 21X (FIG. 18) to call the parent. For example, a four-year old child left in the attended gym nursery while the parent is working out at the gym can call the parent by touching the single designated button 21X to tell the parent he or she is scared of a bully. The parent is reassured that the child can reach him or her whenever there is trouble.

Approved call-in phone numbers are input 603. The parent configuring the CEIL system will input any phone numbers that will be allowed to call into the CEIL system. To protect the privacy of the child and family, the CEIL system will, by default, not answer any incoming phone calls except for calls from designated phone numbers specifically input into the configuration interface (unless configured otherwise). If a non-designated phone number attempts to connect to the CEIL system, the CEIL system or the cellular carrier system may be configured to play a recorded message similar to a voice mail message. The recorded message may say, for example, "This phone does not receive calls" or "This phone number is not active" or the like. The designated call-in phone numbers input into the configuration interface will preferably include one or both parents' cell phone numbers, work numbers, home numbers and any other phone numbers from which the parents might call. The designated call-in phone numbers will also include the phone numbers of any other family members or friends that are permitted to call in to talk to the child.

Each designated call-in number may be assigned 604 particular permissions. The ability to set permissions allows parental control over the length and frequency of incoming calls. For example, a grandparent or non-custodial parent might be limited to three phone calls a day for five minutes each call; this allows communication to be maintained, yet is not lengthy enough to overwhelm the child or to infringe on the child's other activities.

Another configuration process allows the parent to verify pre-set cue prompts or to alter the pre-set cue prompts 605. A cue prompt is manually dialed by the person calling, after the call-in number is connected to the CEIL system. The cue prompt dialed is used by the person making the incoming call to cause or prompt the CEIL system to perform a certain action. The prompted actions may vary depending on the installed software and applications. For example, a cue prompt such as *777 may activate an un-mute announcement while *555 may cause the camera to zoom out to a wider angle. Optionally, cue prompts may include pre-designated SMS text messages.

Further, the configuration interface allows the parent to create 606 an un-mute announcement. The un-mute announcement is an auditory and/or visual message signifying to the child that the incoming caller, who is now connected, will be talking. The un-mute announcement may be a vocal message (such as, "Mommy is calling"), music, ringtone or other greeting. The visual un-mute announcement may be an image or picture of the caller. (For example, a picture of Dad appears on the screen 25 when Dad calls.) The un-mute announcement assists the child in realizing someone is going to speak, so the parent or other incoming caller does not startle the child. The un-mute announcement may be created 606 either through the CEIL system configuration interface or created 606 remotely from the CEIL system by phoning into the CEIL system and dialing a specific message-record cue prompt such as *559 to enter the cellular un-mute announcement configuration process. Thus, with the dial-in cue prompt, the parent may allow relatives and friends with designated call-in numbers to likewise create their own un-mute announcements by the call-in remote system. For example, the grandmother could call the CEIL system, dial the message-record cue prompt *559 and record her voice saying, "This is Grandma calling, Rylee." Then each time Grandma called, the CEIL system would announce her call with the recorded voice message instead of with a ringtone.

Another configuration process that can be allowed in the configuration interface is the assigning or corresponding 607 of particular un-mute announcements to the designated call-in numbers. During the initial setup, no relative or friend can yet have used the CEIL cellular system to call in to set up a recorded message, therefore, the parent can assign pre-recorded generalized messages, ringtones or music to particular call-in numbers. For instance, the parent may assign a traditional French nursery rhyme to the call-in number of a French grandparent. If the message-record call-in remote system is not used to change this assigned un-mute announcement, it may continue to be used.

Also, in FIG. 20, the CEIL system provides the ability to configure the call-out option 608. The call-out function allows the child to phone out to a designated call-out number. The call-out function 608 can be modified to adjust to the age of the child. Although an infant is not capable of using this functionality, a four-year-old child left with a babysitter can easily use a single button that is set to speed dial his mother in case of emergency. An eight-year old child needs a different configuration of the call-out function 608; thus the parent can use the call-out function 608 configuration interface to allow the eight-year-old child to call any of multiple relatives, friends and classmates using speed dial buttons or an on-screen dial pad. The CEIL system allows the parent to enable, disable, restrict and configure the call-out function.

FIG. 21 illustrates a continuation of the exemplary cellular configuration processes, emphasizing configuration steps that are focused on an older child. Particularly as the child grows older or when the CEIL system is purchased for an older child, several different, extended configurations may be needed.

The parent can define multiple relationship categories 610 reflecting the different relationships that different contacts have with the child. Each of the defined multiple relationship categories 610 may have defined restrictions and allowances set. For example, the parent may define a classmate category, a teacher category, a close family category, an extended family category and a parent category. Then the parent can set the parameters for each relationship category. For example, the parent may allow classmates to call into the CEIL system and the child to call out to the classmate from 3:00 p.m. until 8:00 p.m. each evening. Thus, the classmate relationship category will be assigned this restriction. But the parent category would be assigned no restrictions, allowing incoming and outgoing communication twenty-four hours every day.

Though using the relationship categories to facilitate setting group restrictions 611, the call-in phone numbers will preferably still be entered by the parent. This limits unknown callers and provides safety for the child. However, optionally, for older children, this limitation may be removed. For example, removing the requirement for the call-in numbers to be pre-entered into the configuration interface before using may be advantageous to allow more classmates and friends to contact the child. Optionally, the CEIL system can add any outbound number that is dialed using the on-screen dial pad manually by the child to the designated call-in number list.

Another configuration option is to enable, restrict or disable texting 612. With older children, the parent may decide to allow texting, but restrictions and allowances can be placed based on the relationship categories 610. Similarly, the length of calls allowed for each of the relationship categories 610 can be limited 613.

The option to enable and disable the auto-answer function 614 can be provided to parents, as this feature may not be needed or desired by older children.

The ability to enable, restrict and disable Internet access 615 via the cellular system 30 may be provided. This may be desired to allow the child in elementary school to perform research for papers and other class work. However, parental control of the amount of time of usage and of content 616 may be provided, allowing the parent to block sites or sets of sites. Similarly, the parent may be given the option to enable, restrict and disable 617 the camera feature, with the option to correspond each relationship category 610 or each call-in number to a particular permission.

6. Alert System 120 Components—FIG. 22

The alert system 120 (FIG. 22) includes the display screen 25 and speaker(s) 18, which, in combination with the cellular system 30 and computer system 40 (FIG. 19) enable the parent to set notifications, reminders, alarms and an anti-wandering alarm signal. The parent can set and/or configure these alerts through the alert configuration interface 900 of FIG. 23 and the child's schedule configuration interface of FIGS. 38-40. The alerts may be audible alerts produced by one or more speakers 18 or may be visual alerts displayed on display screen 25. Optionally, an older child may use the touch screen-type display screen 25 to access the configuration interface 900, for example, to set a wake-up alarm.

The parent may wish to give the child programmed reminders concerning tasks, chores or events. The alerts can be musical recordings, digital sounds, alarms, vocal recordings or the like. For example, the parent may record a vocal recording to remind the child to feed a pet, to give instructions about a chore, to prompt the child to finish homework before playing or to remind the child to prepare for a special event at school. Or, the parent can set soft music to play to gently wake a child for preschool.

The anti-wandering alarm signal can be used by the parent to locate a child who has wandered off. The anti-wandering alarm signal is a loud sound produced by the speaker(s) 18 of the CEIL system and instigated by the parent. For example, there may be difficulty at a busy theme park in locating a child who has merely moved around a corner. Parents can use their mobile device to call or text the child's CEIL system. When calling, the parent can then press a specific cue number designated to activate the anti-wandering alarm function on the child's CEIL system. When texting, a specific text message can be designated as functional, such as texting "alarm." (The child may be holding the cell-enabled doll companion, carrying the doll companion in a backpack or the like.) The loud, distinctive, audible signal allows the parent to instantly locate a child in a crowd. The anti-wandering alarm signal functionality can be made available in the initial setup or as a downloaded application. A unique anti-wandering alarm may be chosen from among numerous provided sounds.

Figure 23:
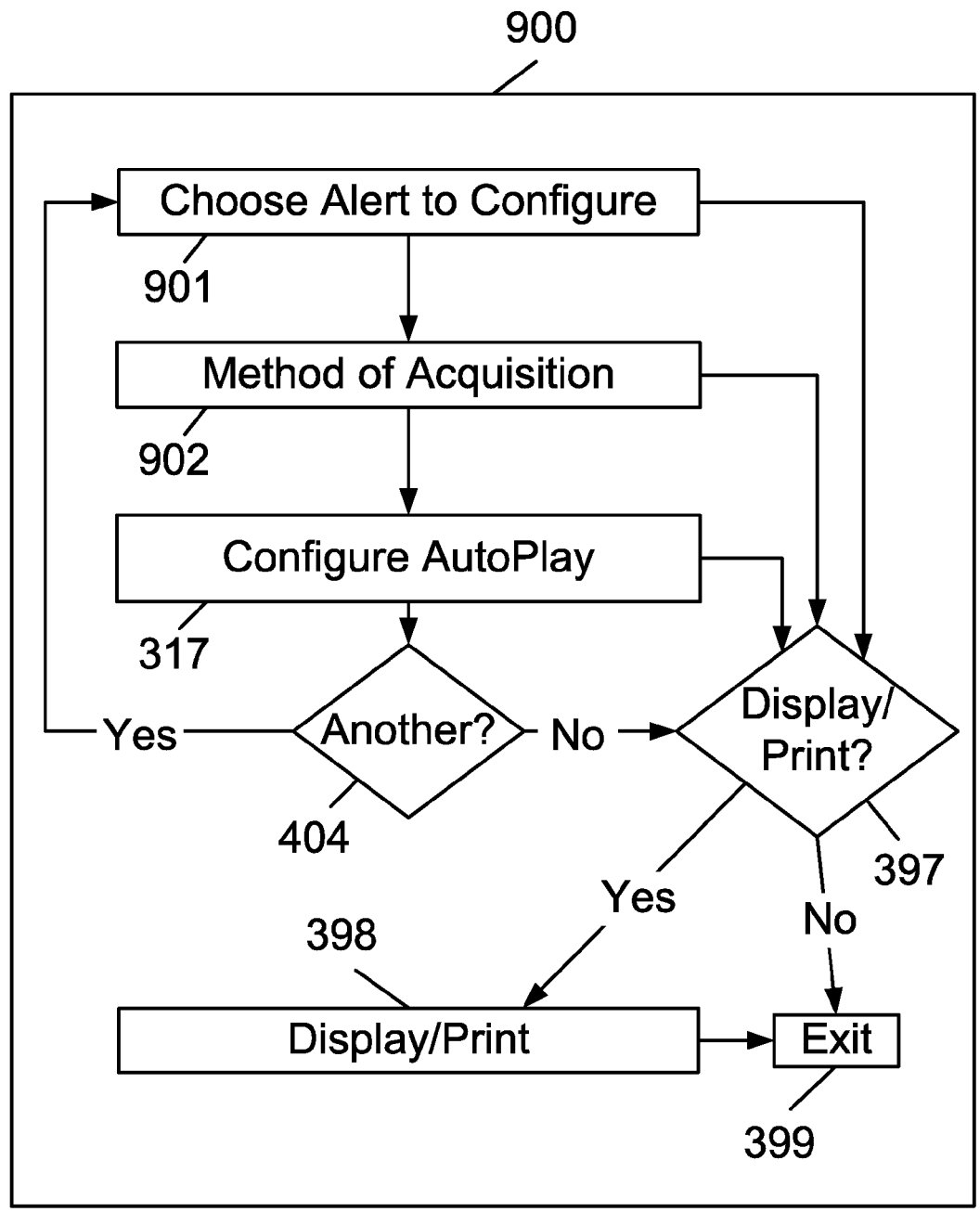
FIG. 23 is a schematic showing an exemplary configuration interface for configuring the alert system of the doll companion system of the present invention.

6.1 Configuration of Alert System—FIG. 23

Turning to the alert configuration interface 900 of the alert system 120 shown in FIG. 23, the parent user accesses the alert configuration interface 900 by any of the parent-access methods described in relation to FIG. 14.

The parent chooses the alert 901 to configure; it may be any one of the various alarm/alert types (notification, reminder, alarm and anti-wandering alarm). The alert or alarm signal can be configured with a unique, chosen sound clip. The parent then chooses the method of acquisition 902. The methods of acquisition include retrieving a stored sound/video clip, downloading a new sound/video clip, or recording an alert sound/video clip. The parent then determines when and how often (752, 754, FIG. 38) the alert should be played to the child and adds this autoplay 317 "alert event" to the child's daily schedule 745 (FIG. 40). At most or all times during the configuration process, the parent is offered the option to view or print 397 the child's schedule 745 to assist the parent in determining the layout and time slots.

The parent chooses whether to configure another 404 alert. If no other alert is to be configured, the parent is preferably offered the option 397 to display and/or print the child's daily schedule with the events listed. The parent can display and/or print 398 the child's schedule to verify the number and frequency of any alert events, educational events and entertainment events. When finished with configuration changes the CEIL system is updated and the parent exits 399 the configuration interface.

7. Audio/Visual Monitoring Systems 90A, 90B, 130 Components—FIG. 24

Figure 24:
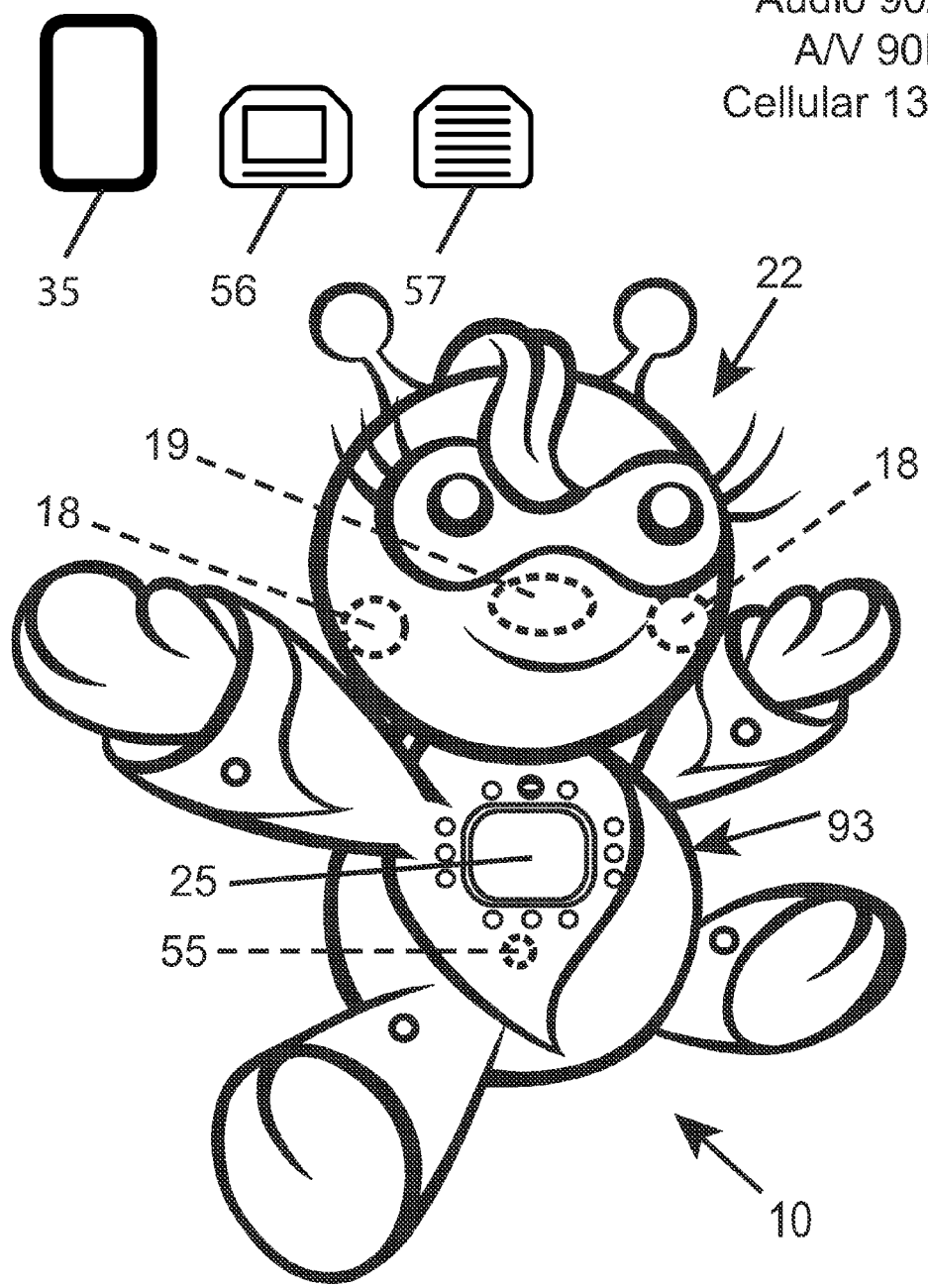
FIG. 24 is a perspective view showing the components of the audio/visual system disposed on and within the doll/toy housing of the doll companion system of the present invention.

As seen in FIG. 24, the audio/visual monitoring systems of the CEIL system use the microphone 19 and camera 55 as input devices and use the speaker(s) 18 as an output device. Optionally, display screen 25 can be used as an output device. The microphone 19 (shown in head area 22) and camera 55 (shown in stomach area 93) are disposed in a location that allows them to obtain audio and visual data of the area around the CEIL system. The speaker(s) 18 output the parent's voice; optionally, the screen 25 may output a still or video image of the parent.

Figure 25:
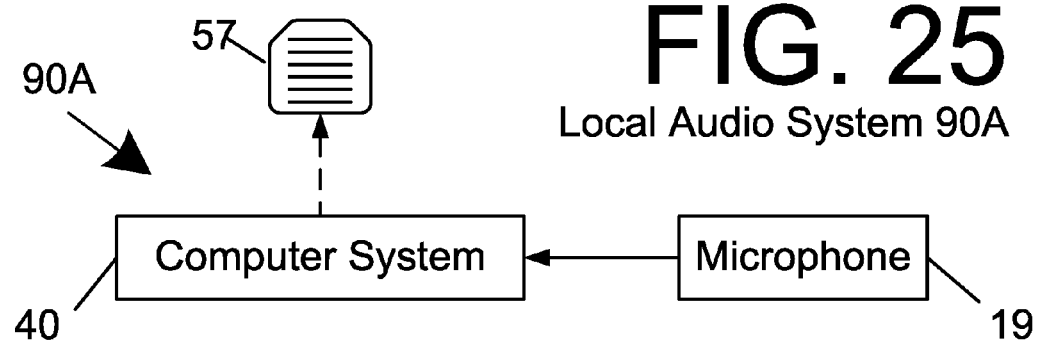
FIG. 25 is a schematic showing the organization of components of the local audio system of the doll companion system of the present invention.
Figure 26:
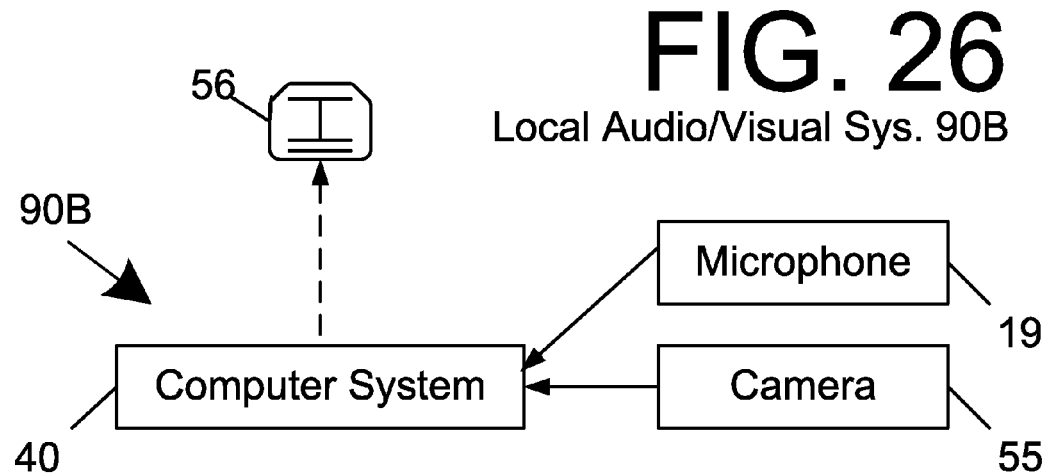
FIG. 26 is a schematic showing the organization of components of the local audio/visual system of the doll companion system of the present invention.
Figure 27:
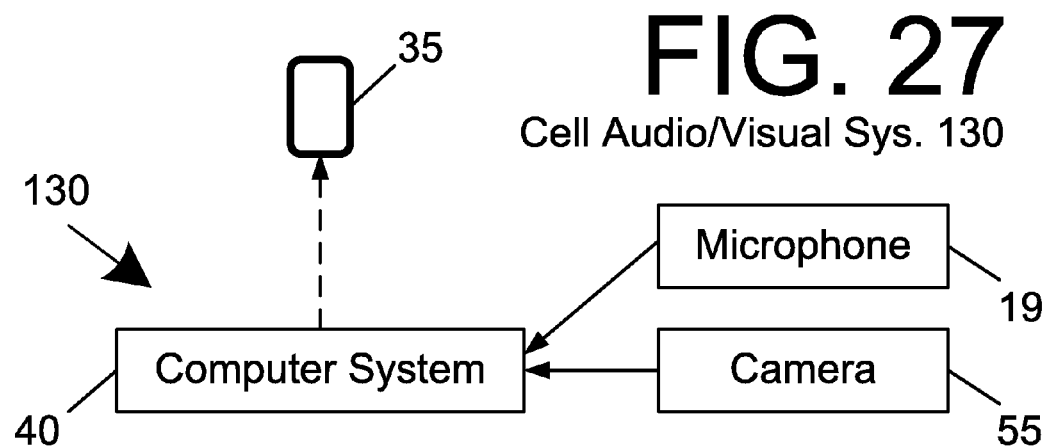
FIG. 27 is a schematic showing the organization of components of the cellular audio/visual system of the doll companion system of the present invention.
Figure 28:
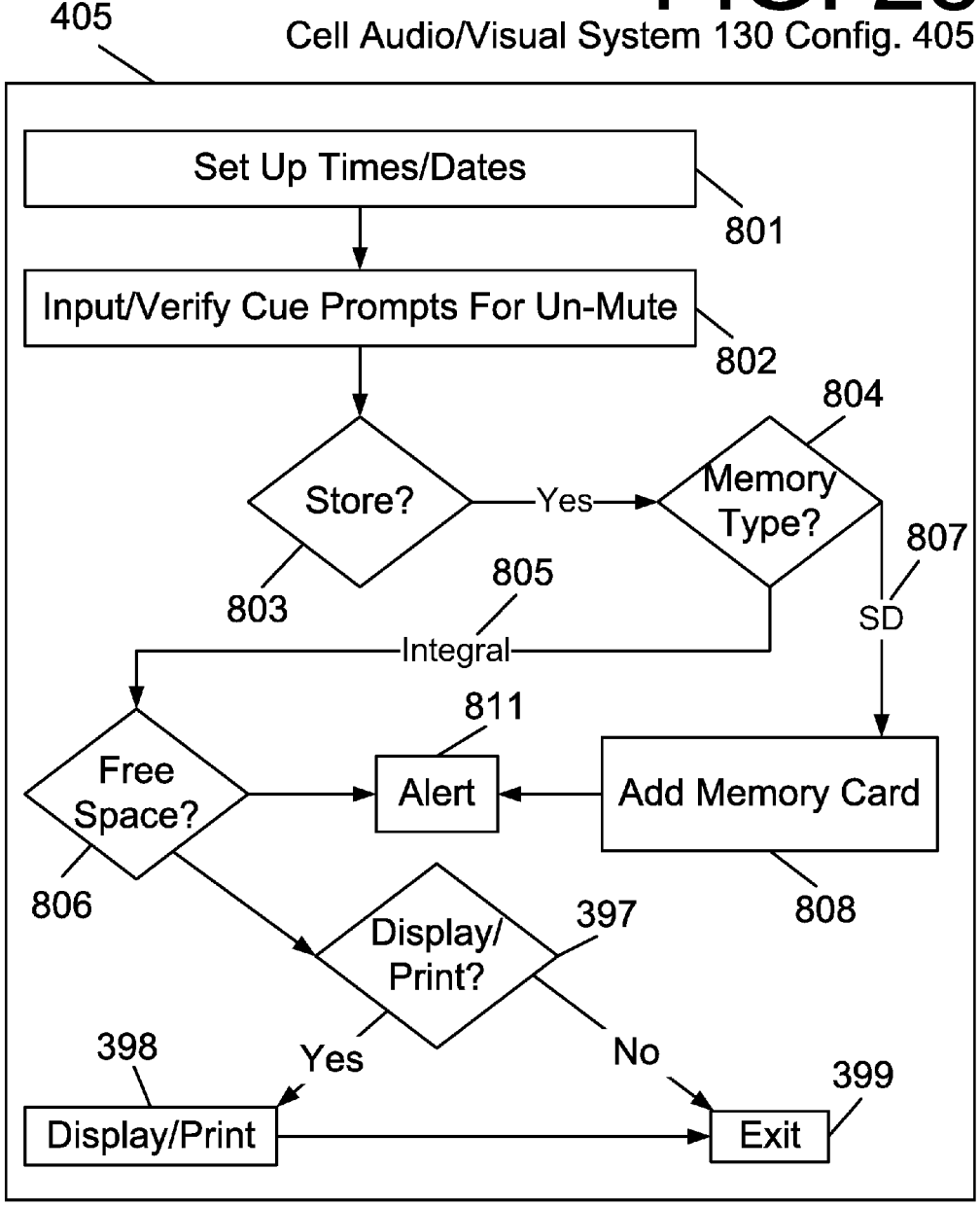
FIG. 28 is a schematic showing an exemplary configuration interface for configuring the cellular audio/visual monitoring system of the doll companion system of the present invention.

The audio/visual monitoring systems 90A, 90B and 130 of the CEIL system include three types of receivers 56, 57, 35 used in the transmission modes, illustrated in FIG. 25, FIG. 26 and FIG. 27, respectively, for providing real-time surveillance of the child's environment. Additionally, the data can be stored for later review. These operating modes include a local audio monitoring mode (FIG. 25), a local audio/visual monitoring mode (FIG. 26) and a cellular monitoring mode (FIG. 27). These transmission modes can be enabled and configured by the parent by accessing the configuration interface (FIG. 28).

The local systems 90A, 90B use a separate local audio receiver 57 or local audio/visual receiver 56, respectively, allowing the parent to use the CEIL system locally, such as within a home, for continuous monitoring without incurring any additional cost that may be associated with use of the cellular system 30. The local audio receiver 57 and local audio/visual receiver 56 may be free-standing receivers similar to conventionally available baby monitor receivers. The transmission of the data to the local receivers 56, 57 may be by radio transmission, by use of a home wireless network or other wireless transmission methods as are known, or become known, in the art. For example, the transmission may be similar to the transmission to a standard baby monitor.

The microphone 19 is operable to capture sounds from the child and the child's environment. The computer system 40 receives the sound data from the microphone 19. The sound data are used to allow the parent to hear the child and the child's environment. The audio data can be stored in the memory of the CEIL system for later review. Additionally, the sound data are available for real-time transmission to the parent.

The sound data may be wirelessly transmitted to the local audio monitor receiver 57, as shown in the local audio monitoring mode of FIG. 25. Optionally, the sound data can be transmitted through the cellular system 30 to the phone 35 of the parent as shown in the cellular monitoring mode 130 of FIG. 27.

In the local audio monitor mode 90A of FIG. 25, the audio data from the microphone 19 are wirelessly transmitted to the computing system 40 which transmits the data through a transmitter in the doll companion to the audio receiver 57.

In an exemplary use, the parent places a doll companion in an infant's crib. The doll companion may optionally be supported in a charging saddle.

The parent can place the audio receiver 57 in a different room of the house, yet hear the child's environment through the audio monitor without use of the cellular network.

The camera 55 allows remote video surveillance of the child and the child's environment. The combination of the data from the microphone 19 and from the camera 55 (or the data from either alone) can be supplied to the parent in real-time and/or recorded for later review. The camera 55 is preferably a color camera of the type that is widely available in video baby monitors and web cameras. Optionally, the camera 55 may pan and/or zoom (which can be controlled by the parent remotely by cue prompts input through the parent's cell phone). Optionally, multiple cameras 55 can be disposed in multiple areas of the doll/toy housing. Including multiple cameras 55 provides a greater likelihood that at least one camera 55 would be aimed in a direction of interest for video surveillance by the parent.

Real-time audio/video surveillance is provided by the audio/visual monitoring system 90A, 90B, 130 of FIGS. 25-27. The audio/visual monitoring system 90 may be enabled, disabled and configured for use in the audio/visual configuration interface (FIG. 28). When enabled, the CEIL system transmitter will transmit both the audio and video data to the local video/audio receiver 56 having both a video display and speaker. The parent places the local video/audio receiver 56 in any room within range of the transmitter and can continuously view and hear the child in real-time without use of the cell phone system 30. Preferably for infants, the doll companion is placed in the charging saddle, allowing the system to charge while the camera 55 is held in the proper position to view the child.

Additionally, the audio and/or video data are available to the parent through the cellular monitoring mode 130 (FIG. 27). The remote parent can observe the child in substantially real time through the cellular connection, watching the child on the display screen of his or her phone. Using this cellular monitoring mode 130, if a parent at his office computer sees that his child at home is about to pull a pot of boiling water off the stove, he can immediately give a real-time voice warning.

To initiate this video monitoring, the parent calls the dedicated CEIL phone number and is immediately connected to the video and audio feed, without any indication from the CEIL system to the child or to others in the child's environment that video and audio surveillance is occurring. The parent retains the ability to announce him or herself. The CEIL system preferably will hold the parent on mute for convenience in remote surveillance until the parent dials a specified cue number. Depending on the cue number dialed or on the initial setup (FIG. 20), the CEIL system may then announce the parent is calling or may merely un-mute the parent so the parent is heard by the child and those in the child's vicinity.

In addition to viewing the child via the cellular system and local system, applications can be offered to allow the parent to view the child on a tablet, laptop or desktop computer, through use of any of a variety of cellular and Internet connectivity options.

Optionally, the recorded video and audio data may be stored for later access and review. The integrated, onboard memory 43, FIG. 19 (utilized by the processor 47) can be configured (via audio/video configuration interface, FIG. 28) to store the recorded video and audio data. At a later time, such as at the end of the day, the parent can download the stored video and audio data onto his or her computer through the toy-to-computer connector 77 (FIG. 18), such as a USB connector.

Alternatively, a removable memory card for storage of the recorded video and audio data can be included in the system. The memory card interface 97 (FIG. 18) is configured to accept an add-on memory storage unit, such as an SD card, micro SD card, flash memory or other types of removable memory. Though the onboard memory can be used to store recorded audio/visual data, the removable memory provides advantages, such as easy removal of memory storage units, convenient storage of removed memory storage units, reduction in memory demands on the onboard memory (if the installed onboard memory 43, FIG. 19, becomes too full, the processor 47 will not be able to operate efficiently), and unlimited space as memory storage units may be installed and removed indefinitely. For example, a four GB SD memory card can store approximately eight hours of real-time audio/video recording. So the blank SD card could be installed by the parent in the morning before leaving the child with a babysitter during the day, and then retrieved after work with the day's audio and video recording stored thereon.

Thus, through the use of the audio/visual monitoring system integrated with the cellular communication, if the child becomes separated from the parent, the parent can see that there is a picnic table beside the child and, then, can say to the child, "See the red picnic table in front of you? Sit there and wait. I will come right away."

7.1 Configuration of Audio/Visual System—FIG. 28

FIG. 28 illustrates the exemplary steps in the configuration of processes and settings of the audio/video systems, particularly the cellular audio/video system 130. The audio/video system not only provides real-time monitoring via the cellular system 30, but, optionally, can store recordings. The audio/video configuration interface 405 of FIG. 28 allows configuration of the storage and recording of the audio and visual data.

The parent can enable or disable the audio/video system and/or set up or pre-configure start times and dates 801 (such as setting the audio/visual system to record during times a babysitter is employed). These start times and dates can be input into the child's schedule (FIG. 40). The CEIL system may allow the parent to verify or input cue prompts to play the un-mute announcement 802.

The audio and visual data are received by the computing system 40 (FIG. 17) from microphone 19 and camera 55. The audio/video configuration interface offers the option to store 803 the data. If the parent chooses to store 803 the data, the option of memory type 804 is offered. If the parent chooses the integral, onboard memory 805, the CEIL system preferably checks the free memory space 806 and alerts 811 the parent of the approximate hours of recorded data that can be stored on the available space. If the parent chooses the removable memory 807, the CEIL system preferably alerts the parent to add a memory card 808, if a blank one is not currently installed. If the installed memory card 808 is not blank, the CEIL system preferably checks the free memory space and notifies the parent. An option to display and/or print 397 the child's schedule 745 (FIG. 40) is offered. Displaying 398 the schedule may assist the parent in selecting correct times.

8. GPS/Location System 60 Components—FIG. 29

The CEIL system is designed for use with an optional or add-on GPS/location system 60 using the Global Positioning System (satellite-based global navigation system) that allows accurate location tracking. Additionally, the GPS/location system may pair cell tower and Wi-Fi data in tandem with the GPS data to pinpoint the location more efficiently. The doll companion is configured with an operational GPS system, including a GPS receiver configured to determine the geographical location of the doll companion 10 based on received satellite signals or configured to receive signals that are transmitted to the computer system 40 to determine the geographical location.

A safety band 66 (FIG. 29) that is wirelessly connected to the computer system 40 is worn by the child, such as on the arm or leg. The doll companion is configured to alert the parent or other authority, if the safety band 66 is separated from the doll companion or removed from the child. The safety band 66 is preferably tamper resistant, such as with a keyed lock 68, preventing the removal of the band 66 without generating an alert. Thus, the function of the band 66 is to trigger an alert if it is separated from the CEIL doll companion or forcibly removed. For this purpose, the band 66 does not require GPS tracking capability nor cell phone capability, but is configured with a portion of a wireless band disconnect system, with the doll companion configured with a corresponding, complementary portion of the wireless band disconnect system. The wireless band disconnect system can use any short-range wireless connectivity, such as Bluetooth®, RFID, Near Field Communication (NFC) or the like. Each of these wireless communication systems is sufficient to accomplish the purpose of pairing the safety band with the CEIL system. Preferably, RFID technology or NFC is used to eliminate the need to charge the safety band. An advantage of NFC is that it may be used for the wireless band disconnect system, as well as for the smart card system of FIG. 36.

Figure 30:
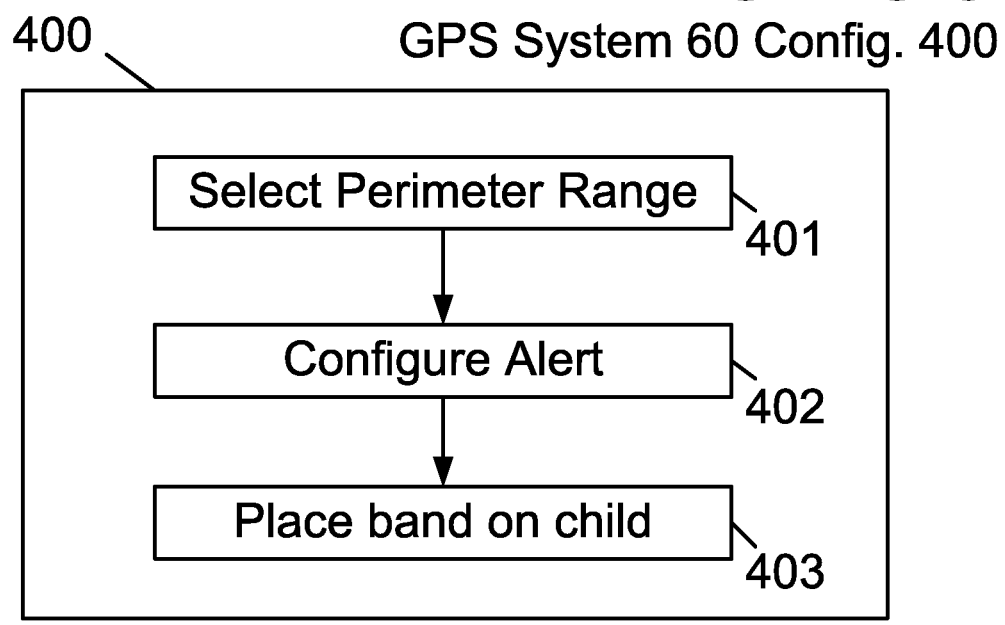
FIG. 30 is a schematic showing an exemplary configuration interface for configuring the GPS system of the doll companion system of the present invention.
Figure 31:
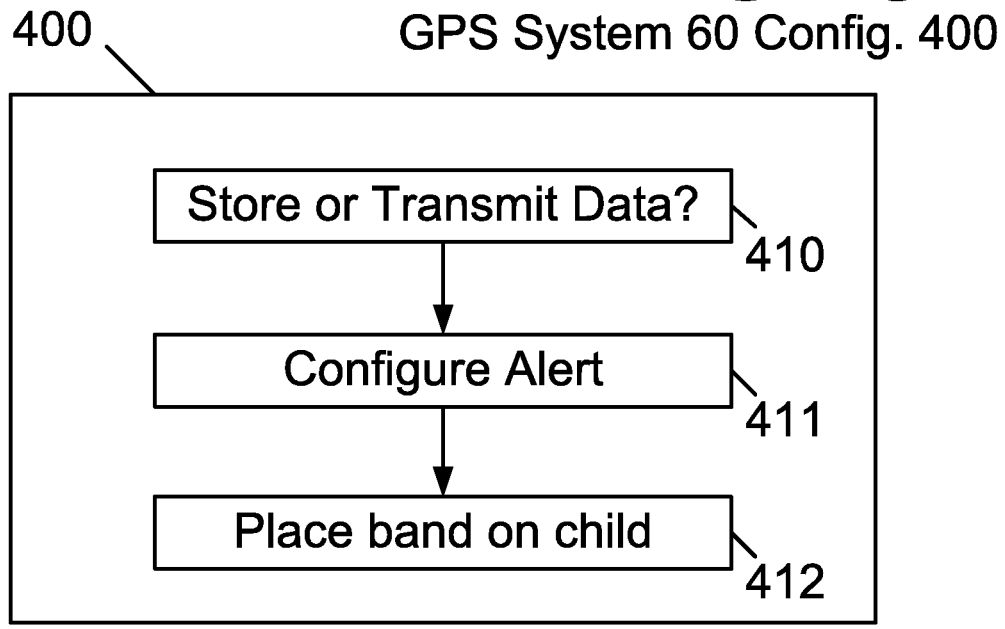
FIG. 31 is a schematic showing an exemplary configuration interface for configuring the GPS system of the doll companion system of the present invention.

8.1 Configuration of GPS System—FIGS. 30-31

The GPS system 60 includes two configuration protocols, a perimeter type and a location tracking type, which may be used independently or in combination. Both protocol types include a notification system to alert the parent. Both types include the safety band 66 and the GPS receiver 65 within the doll companion itself.

In the perimeter GPS protocol (FIG. 30) the parent can set boundaries or a perimeter around an allowed area. The perimeter may be set by entering a locus (a center point designating the purported location of the child, such as a home address, a preschool address, or the like) and then by entering a permitted distance from the specified locus. For example, the parent may expect the nanny may, at times, take the child to the nearby neighborhood park, so may set the permitted distance as one mile from the locus (the house address). As shown in FIG. 14, the perimeter may be set by accessing a configuration interface provided by installed software on a computer connected to the doll 102, by accessing a configuration interface website 130, by phoning a customer service 104, 105, by inputting the perimeter directly into the doll companion touch screen 25, or by SMS 106. If using SMS 106 the doll companion, a configuration protocol allowing the parent to text the parameters can be provided. For example, the parent can text "Locus=1234 Oak St., Miami, Fla." to establish the locus; then the parent can text "Distance=1 mile" to establish the permitted perimeter, the distance from the locus.

If the doll companion is taken beyond the set perimeter or if the band 66 is separated from the CEIL system, an alert will be sent via the cellular system 30 to notify the parent. Upon receiving the alert, the parent can immediately use the audiovisual system to begin full audio and visual surveillance of the area.

As shown in FIG. 30, the parent first selects a locus and then a permitted distance to establish a perimeter range 401. Optionally, instead of a locus and permitted distance, the parent can outline an allowed area on a map of the area of interest. This can be done visually if accessing the configuration interface through computer software, a website or the touch screen 25. Or outlining an allowed area may be done orally through use of the customer service center; this option is advantageous when on a trip as only the parent's cell phone is required.

The parent then configures the alert 402, with at least one notification sent by the cellular system 30. The type of alerts sent can be configured, such as enabling a text message, voice call, alert ringtone or a combination. The number and type of alerts sent can also be configured, such as configuring the alerts to be sent to both parents. For example, if the parents are traveling with the child who is left with a babysitter at a hotel, the GPS system can be configured to notify both parents by both text messages and/or voice alarms if the child is separated from the doll companion or if the doll companion is more than fifty feet from the hotel room. The band 66 is then placed on the child 403.

In the location tracking GPS system (FIG. 31) the parent configures the storage and transmission 410 of the GPS location data. For example, the parent may configure the GPS system to record location data every five minutes and transmit it as a text message every hour from the CEIL system using cellular connectivity to the parent's cell phone. Or the parent can configure the GPS system to record location data each minute and transmit it to a web-based (optionally, fee-based) service that allows the parent to securely access the web-based service website to view the recorded location data.

The type and recipient of the alerts are configured 411. The band 66 is placed on the child 412. If the band 66 is removed from the child or if the doll companion is removed a pre-determined distance from band 66, an alert is sent according to the configuration settings.

Though an alert is sent if the doll companion 10 is thrown down and the child (with band 66) removed from it, there will be no GPS tracking identifying the child's whereabouts once separated from the doll companion 10. However, the audio/visual monitoring system may be immediately employed by the remote parent to hear and view the area around the doll companion. Though rapidity of response is essential when the child is separated from the doll companion 10, the immediate viewing of the area provides immediate information for the parent and others, such as law enforcement members.

Optionally, the GPS system 60 and the health/SIDS system 70 may both make use of the band 66. For example, a health sensor 71 that determines movement or temperature may be incorporated into the band 66.

9. Health/SIDS Monitor System 70—FIGS. 32-33

Figure 32:
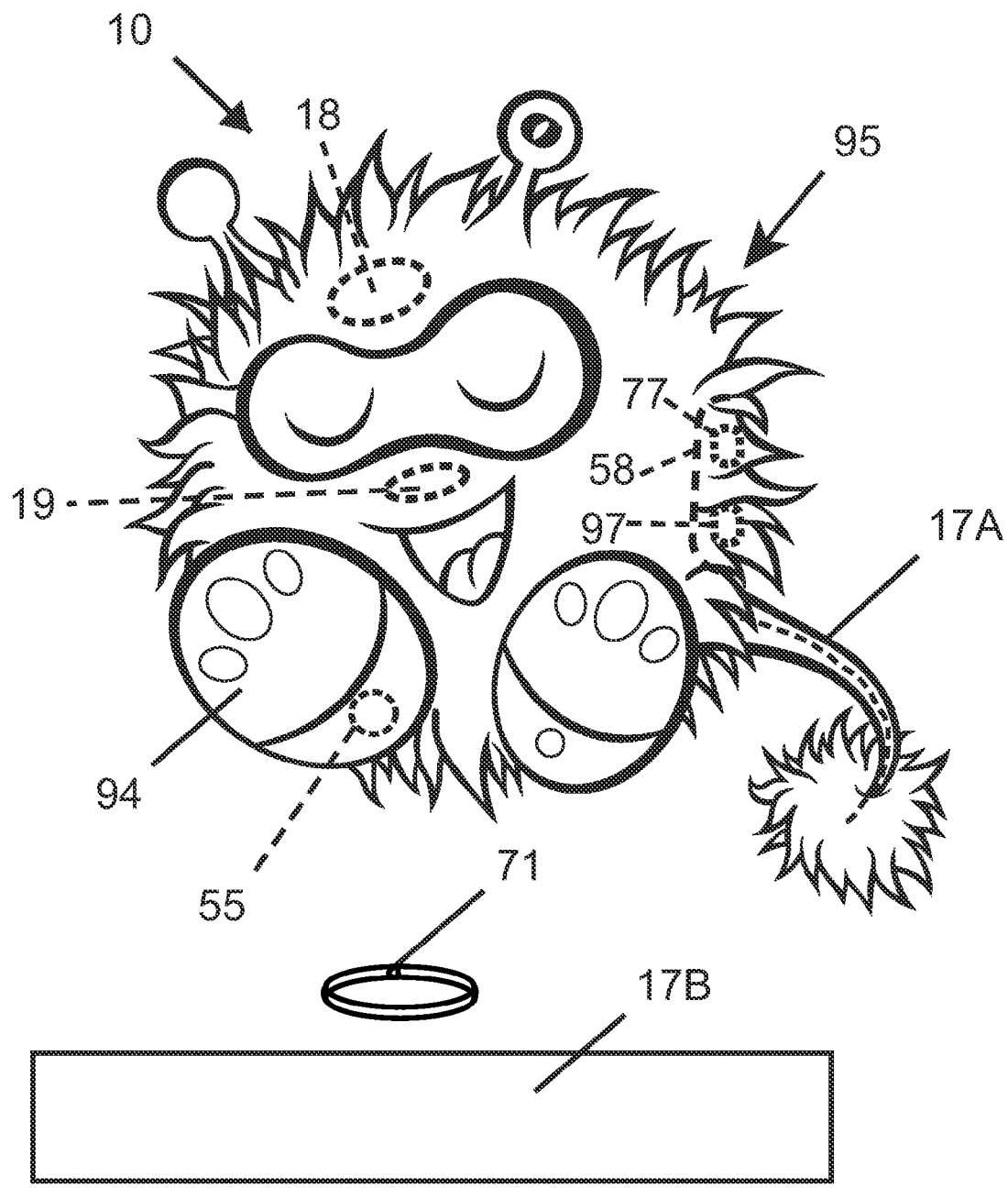
FIG. 32 is a perspective view showing the components of the audio/visual system disposed on and within the doll/toy housing of the doll companion system of the present invention.
Figure 33:
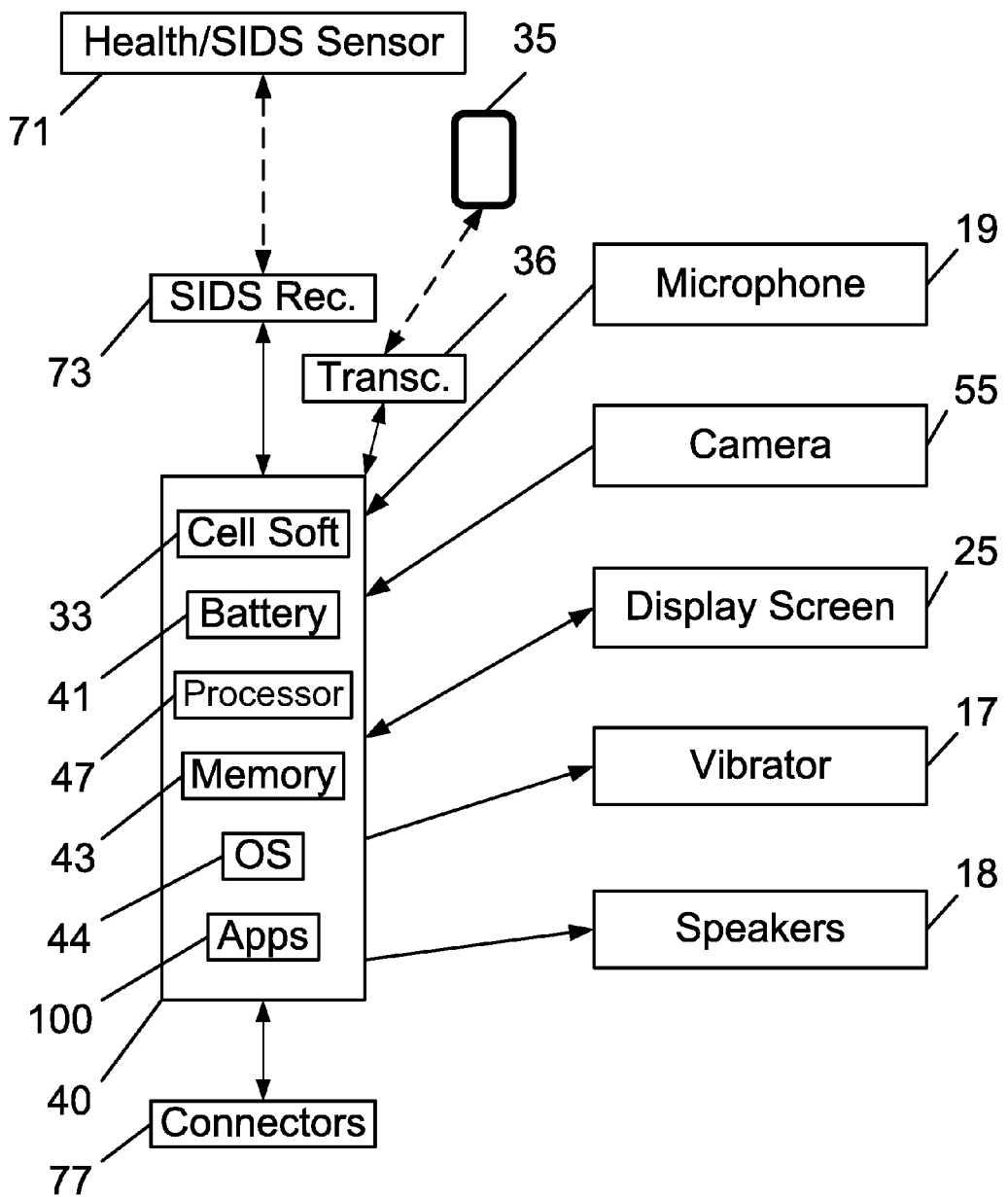
FIG. 33 is a schematic showing the organization of components of the health/SIDS monitoring system of the doll companion system of the present invention.

As shown in FIGS. 32-33, the health/SIDS monitoring system 70 includes a health sensor 71 connected wirelessly to a health/SIDS receiver 73 that is operably attached to the computer system 40. The health/SIDS monitoring system 70 uses the cellular system 40 to send alerts or to transfer health data to the appropriate health manager. The health/SIDS monitoring system 70 also preferably utilizes the data from microphone 19 and camera 55 to allow the parent to monitor the child. Vibrator(s) 17, display screen 25 and speakers 18 may also optionally be used to stimulate or alert the child.

The health monitoring system 70 is available any time of the day or night to sense the condition of the child, to detect if the subject's condition falls outside a normal range, and to activate an audio alert signal and/or cell phone emergency call to elicit help. Optionally, health-related data can be stored, allowing a medical professional to view the health history of the child.

The health monitoring system 70 is used to monitor a child for health-related issues (such as to detect sleep apnea or SIDS episodes, to measure vital signs, and/or for other medical reasons) and to alert the parent or a medical professional through the cellular system 30 to any health issues detected. As shown in FIGS. 32-33, the health monitoring system 70 includes a health sensor 71 configured to obtain sensor data. The health sensor 71 may be directly connected to the computer system 40, but is preferably wirelessly connected. Preferably, a standard radio frequency wireless technology is used, such as Bluetooth®, but optionally, an infrared transmission technology can be used. For redundancy, primary transmission may be by radio frequency with a backup infrared transmission, thus assuring transmission in cases of radio frequency interference.

When wirelessly connected, the sensor 71 is configured with a sensor-data transmitter operative to transmit sensor data to the sensor-data receptor 73, which provides the sensor data to the computing system 40. The computing system 40 is configured (using health/SIDS configuration interface 950 of FIG. 34) to receive the data and act appropriately upon the data.

The health sensor 71 monitors one or more aspects that relate to the child's health and wellness. For example, sensor 71 may detect sound, movement, weight, $CO_2$, temperature, respiratory rate, heart rate, body accelerations or the like.

The need may be based on a pre-existing condition or may be a preventive measure. The health sensor may be incorporated into or may be detached from the doll companion. Any of a variety of sensors currently available to detect or monitor various parameters associated with child health can be utilized with the CEIL system. Optionally, a combination of multiple sensors may be used for specific health issues.

For example, the health sensor 71 may take the form of any of a number of health monitoring sensors, such as (1.) an under-the-mattress sensor pad to detect movement of a sleeping infant; (2.) a sensor that clips to a diaper to assure the baby is moving; (3.) a $CO_2$ sensor to non-invasively monitor the exhaled air from an infant; (4.) an adhesive patch configured to monitor heart rate; (5.) a temperature sensor to monitor the child's temperature while sleeping; etc. Optionally, vibration mechanisms (shown as 17A, 17B) may be included to wake the child in case a SIDS episode is detected. One or multiple vibration mechanisms can be employed. For example, a part of the body of the doll companion 10 can vibrate. Optionally, the vibration mechanism 17B may be incorporated into the under-the-mattress sensor pad to perform a dual purpose.

9.1 Configuration of Health/SIDS System 70—FIG. 34

To set up the health/SIDS system 70, the parent user accesses 299 (FIG. 14) the configuration interface by any of the parent-access methods described in relation to FIG. 14. Turning to FIG. 34, the option is presented to initialize the system or add a new sensor 951. The parameters 952 identifying the normal range for the sensor are entered or parameters associated with the installed sensor 71 may merely be confirmed.

The parent can configure the type of alert 953. These configuration settings include who will receive the alert and how the alert will be sent (phone message or SMS message) if the sensor 71 detects conditions outside the normal parameter range. For example, the parent alone may receive the alert or the parent and an emergency monitoring service, etc. The parent can select to receive health status updates and the frequency of such updates. For example, when a child has a fever, the parent may wish to have the child's temperature sent by text message to the parent's phone 35 every ten minutes.

The parent can also enable and/or configure the recordation 954 of sensor 71 data and the manner and frequency of transmission. At times of a special medical need, a record of such data may be beneficially transmitted by using the cellular system 30 to transmit the data to a doctor's office. Or the data can be stored and transmitted to the parent at recurring times. When finished with the health/SIDS configuration, the CEIL system is updated, whether the configuration interface was reached through the direct connection 102 (FIG. 14), the cellular provider push system 103, the live agent customer service 104, the voice prompt customer service 105, the SMS 106 update or the touch screen 25. The parent exits 399 the configuration interface.

10. Education System 80—FIGS. 35-36

An advantage of the CEIL system is the functionality and expandability provided by the education system 80. The CEIL system provides a platform allowing software developers to utilize the integrated systems to create scalable, expandable applications 100, particularly applications enhancing and encouraging learning by the child. The learning activities can be executed by the parent or by the child.

Parent-planned execution of a parent-selected application 100 occurs when the parent places an educational event on the child's daily schedule; the event may be repeated daily or multiple times within a day, as discussed in relation to FIG. 40. The parent user's ability to place an educational (or entertainment or other event) upon the child's daily schedule to be executed at the specified time allows personalization of the educational activities to meet the child's changing needs.

The child user can self-direct learning by using one of the child activation devices—the smart card system 85, the tactile button(s) 21 and/or a touch screen-type display screen 25, as shown in FIG. 13. By holding the smart card 86 to the card reader, by touching a designated portion of the screen 25, or by touching a tactile button 21, the child executes the child-selected application 100.

Figure 35:
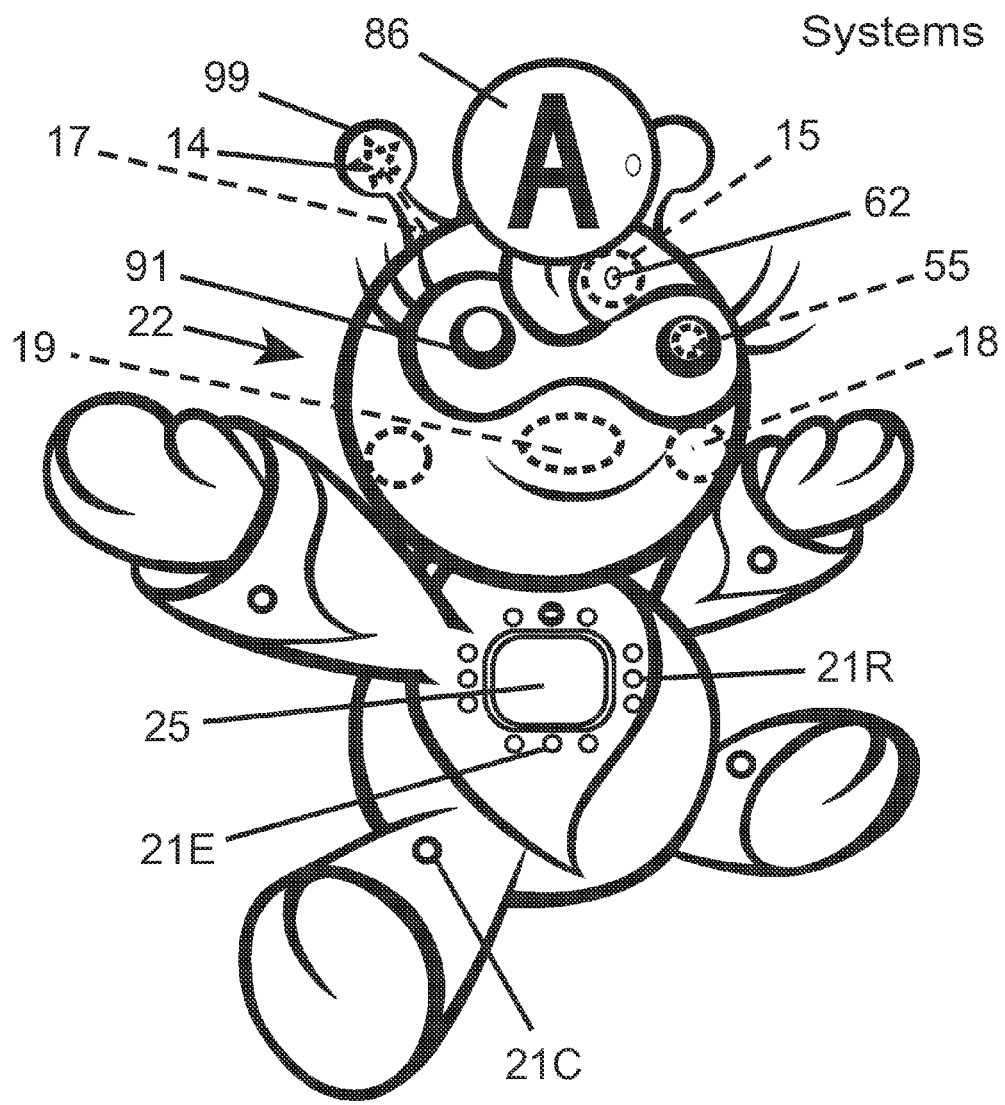
FIG. 35 is a perspective view showing the smart card system with the components of the education system disposed on and within the doll/toy housing of the doll companion system of the present invention.
Figure 36:
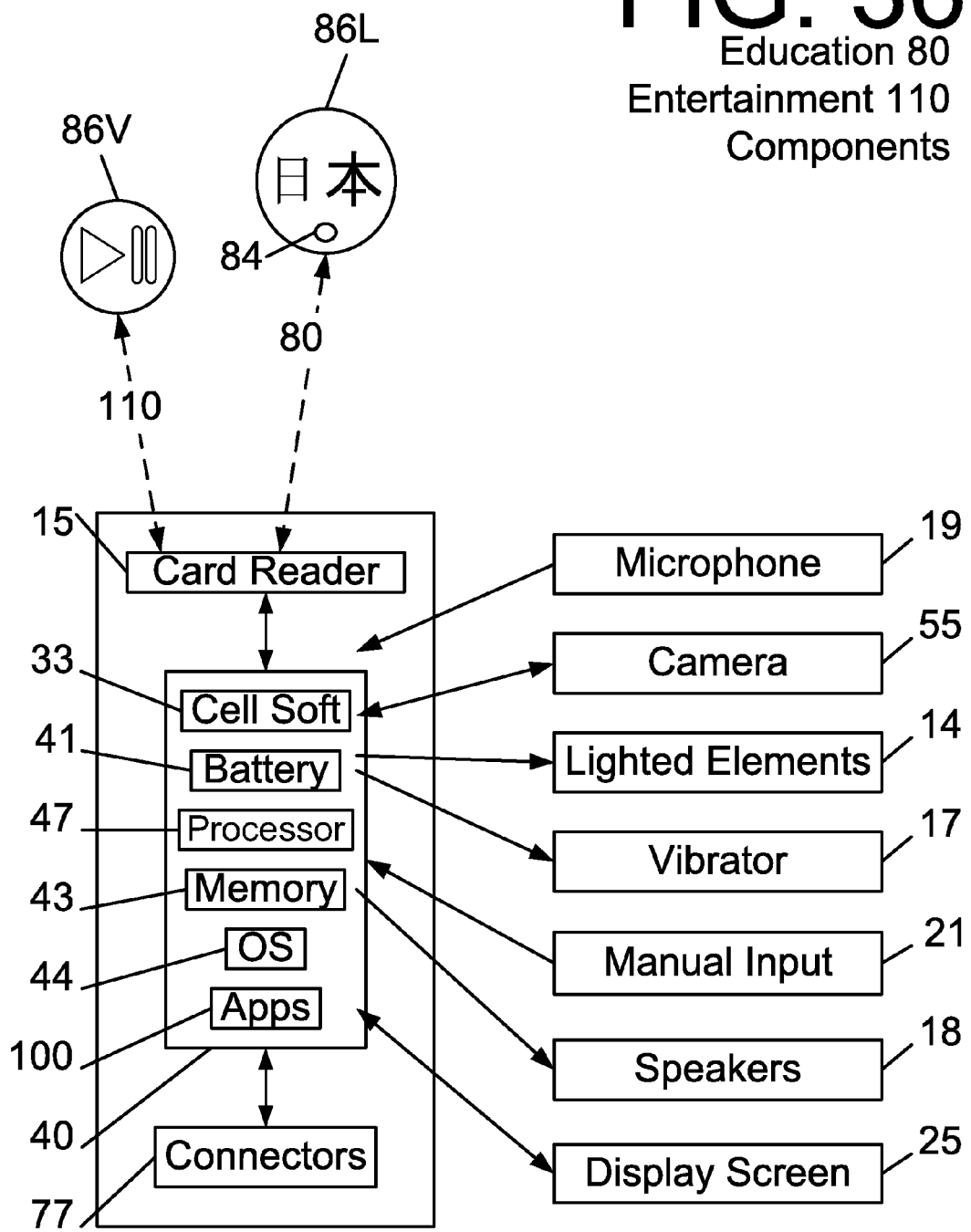
FIG. 36 is a schematic showing the integration of the smart card system with the educational system and entertainment system of the doll companion system of the present invention.

As shown in FIGS. 35-36, the education system 80 may use any of the input and output devices of the CEIL system and may incorporate other subsystems, particularly the app-initiating smart card system 85 with smart cards 86 and card reader 15.

The input devices include the camera 55 and microphone 19. The output devices include lighted elements 14, vibrator 17, speaker(s) 18, touch-type screen 25 and tactile buttons 21. Systems used include the smart card system 85 (smart cards 86 and card reader 15) and software applications 100 developed for the CEIL system. For instance, to reinforce the child's correct response one application may activate the vibration device 17 (FIG. 35) for each correct response, while a second application may activate lighted elements 14, and a third application may play music through speakers 18 plus activate the vibration device 17, flicker the lighted elements 14 and display an animation on the display screen 25.

Some exemplary educational functions and applications that can employ the functionality provided by the CEIL system include the following: development of early hearing and word associational skills; introduction of alphabet sounds, names and examples; educational audio books and movies in selected languages; word pronunciation; introduction to the sounds, intonation and accents of any of a variety of foreign languages; name recognition; teaching of reading through audio instructors; parents' voice commands to maintain voice recognition for the child throughout the day; introduction to various musical styles from Bach to the Beatles customized for the appropriate age groups; foreign language conversion and repeating (described below); advancement of teaching based on the learning progress of the child; and the like.

One exemplary educational function is the learning of languages. As the globalization of the world continues, the learning of multiple languages increases in importance. The CEIL system is designed to allow early introduction of one or more foreign languages, permitting the child to learn to speak from a native speaker in multiple foreign languages, even languages not spoken in the home. The applications for language learning can be purchased through the applications store or one or more language learning applications can be pre-installed at the time of purchase.

In one application, for example, the foreign language conversion and repeating application allows the child to speak words in one language, with the doll companion repeating the child's spoken words back to the child in a designated foreign language. In overview, the microphone 19 receives the child's spoken words and converts this sound to sound data that are transmitted to the computing system 40. The computing system 40 is configured to interpret the child's words, translate the interpreted words into the designated foreign language, and send the translation data to the speakers, which then generate an audible reproduction of the translation data. Thus the child's words are repeated to the child, but in the foreign language. The translation data are preferably previously recorded, stored words and phrases spoken by a native speaker. However, if the appropriate word or phrase is not available in the pre-recorded database of the particular foreign language, computer-generated translation data may be substituted.

Optionally, during setup of the application, multiple languages can be chosen for repeating back to the child. For example, during setup, the parent has chosen for the CEIL system to repeat the child's words in Spanish, and then Chinese. The child says, "Water" in English, and then the doll companion speaks back to the child, "El agua. Shui." Or the CEIL system can be configured to repeat the word in English and in the other language(s). In this case, the doll companion would speak, "Water. El agua. Shui."

A higher level expansion of this foreign language conversion and repeating application is the foreign language conversation function. This function operates in a similar manner, but instead of translating the child's words and then repeating them back to the child in a foreign language or languages, the CEIL system is programmed to respond to the child with appropriate responses in the foreign language.

10.1 Configuration of Education and Entertainment Systems—FIG. 37

The education system 80 is configured (either the initial setup or later reconfiguration) by accessing 299 (by any of the parent-access methods described in relation to FIG. 14) the education and entertainment configuration interface 300 (FIG. 37). During the configuration process, the parent will be able to customize events based on the child's needs and changing schedule by placing timed events onto the child's schedule 745 (FIG. 40). These events specify when the CEIL system is to execute applications, such as applications that are designed to assist in the rapid development of the child's mind, in putting the child to sleep, in teaching him or her various languages, in monitoring specific health conditions, in entertaining the child, etc.

Shown in FIG. 37, the parent searches 310 for an activity provided by an application 100 to educate or entertain the child. The parent then selects 311 the activity to be configured. To assist the parent in selecting the activity, the configuration interface may display menus of categories (such as selections of foreign language, science, math, reading readiness, alphabet learning, music, etc.). The menus may also allow selection by age.

After the parent selects 311 the activity, the method of acquisition 312 is selected. The application providing the activity may already be installed in the CEIL system. The application may be acquired by various means, including the following: (1.) pre-installed at purchase; (2.) available for download (and potentially purchase) from an administrative interface or application store (FIG. 16); (3.) installed from a memory storage device, such as a CD ROM or SD card; (4.) purchased at a retailer with subsequent download; (5.) purchased through the customer service 104, 105 (FIG. 14).

The method of delivery 315 of the activity to the child is then selected. One method is to give 318 the child the pre-assigned smart card 86. A second method is to correspond 319 a generic smart card 86 to a downloaded application, which is then given 318 to the child; for example, the smart card numbered 12e25g98 may be assigned to the particular activity.

The third method is to assign the activity to automatically play ("autoplay") 317 at a particular time and frequency. For example, the parent may choose a "repeat in Spanish" activity. This activity activates the doll companion 10 to use voice recognition software to determine the words the child has spoken, uses translation software to translate the child's words to Spanish, and then plays the translated Spanish words to the child through speakers 18 (the translation played can be of a recording of a native speaker, when available, or a computer-generated voice otherwise). The parent may configure this activity to autoplay 317 from 9 a.m. to 5 p.m. every day except Sunday. Or, for a second example, the parent may choose to have one of the selection of animal videos played a single time at 10 a.m. Monday through Friday. Configuring autoplay 317 adds the particular educational "event" to the child's daily schedule 745 discussed in FIG. 40.

When the parent is finished configuring the activities or at other times, as desired, the parent has the opportunity to display and/or print 397 (not shown in FIG. 37, but as shown in FIG. 23) the child's schedule. When finished, the parent exits 399 the configuration interface.

11. Entertainment System 110—FIGS. 35-36

The CEIL system also excels in providing entertainment for the child. Although some entertainment applications may be initially included in the CEIL system, larger numbers of entertainment applications, including games, will be provided for download from an application store. The entertainment applications can take advantage of the systems and functionality provided by the CEIL system. The entertainment system 110 generally uses the same components as the education system 80. The education and entertainment configuration interface 300 described above in FIG. 37 is used to place educational events onto the child's schedule 745 of FIG. 40.

For the young child, the doll companion can make cute sounds throughout the day or play music or videos pre-selected by the parent. Using the app-initiating smart card system, the child can choose a smart card 86, wave it near the reader 15, and initiate the playing of the corresponding music, video, game or movie on the CEIL system.

Games can be played using the touch screen-type display screen 25 and/or using the tactile buttons 21.

For example, to increase hand-eye coordination, a preschool child may play a "color touch" game using the doll companion 10 with a touch screen 25. The screen lights up with a red color and the system may speak the word "red." The child then touches a red button (such as button 21E). The screen may then play a short animation of a red apple. The screen then lights up yellow and the system says "yellow." When the child touches a yellow button (for instance 21R), the screen may play a short animation of a yellow flower blowing in the wind, and so on and so forth. An "inverse color touch" game can be played in which the child pushes a red button 21E and the screen illuminates solid red and then plays a short animation of a red jacket dancing. Then the child pushes a green button 21C, the screen illuminates green, then plays a short animation of a green ball on green grass. A "hand-eye-coordination color touch" game allows the child to respond to onscreen and/or vocal prompts designating colors to be touched. Buttons 21 may be colored or may change colors. The child can attempt to gain speed in responding to the prompts, increasing hand/eye coordination. As the child becomes faster, a competition mode can allow the child to compete against himself based on time or score or can allow the child to compete against another child a second doll companion.

Two doll companions can use the cellular system 30 to communicate to each other, either by voice only or by voice and audio video chat. This can be done using the cellular system 30 by directly calling from the first doll companion to the second doll companion or by using an application 100 that provides both audio and video (such as Skype® video chat or a CEIL video chat). To use the cellular system 30 for a direct phone call, for example, two classmates each have a doll companion; the cellular configuration interface is configured to allow dialing out and the phone number of each doll companion is input into the other doll companion as a "designated phone number." Each classmate can then dial the phone number of the other classmate and communicate by voice, or, if enabled, by voice and video. If the doll companion is set up with a data plan or WIFI, a video chat program can be used to call without using cell phone minutes.

Both the education system 80 (components shown in FIG. 35) and the entertainment system 110 provide interesting activities and content for the child with significant overlap between the systems.

12. Child's Daily Schedule Configuration—FIGS. 38-40

Though the CEIL system provides many features without setting up a daily schedule 745, FIG. 40, the creation and implementation of a planned daily schedule by the parent user allows the child to receive customized educational activities with a frequency that encourages learning and discourages boredom, while allowing updating of the daily schedule to adapt to the changing interests and age of the child. The parent can create and change the child's daily schedule by accessing (FIG. 14) the configuration interface.

As shown in FIG. 38, the parent chooses 750 the event to be placed on the child's daily schedule. For example, the parent may choose an early alphabet learning program L1, a "time to get ready for preschool" alert A1, a "time for Mommy to pick you up from preschool" alert A2, and a "time to get ready for bed" alert A3. The parent then selects 752 the time (or times) and selects 754 the dates (or days of the week) that the event will be played. For example, the child may have preschool on Monday, Wednesday and Friday, so on those days the A1 alert may be set for 8:00 a.m. with the A2 alert set for noon and with the A3 alert set for 7:00 p.m.

Preferably, at least when using some access modes to the configuration interface, the option to view 397 (or print) the daily schedule is available to the parent at all times during the scheduling of events, so the parent can verify the number, frequency, repetitions and types of scheduled events. For example, when accessing the configuration interface through a computer connected (wired or wirelessly) to the doll companion 102 (FIG. 14), a networked or local printer can be used to print the child's schedule. If a computer is used to access the configuration interface website 103, the view option will be available, and if a local or networked printer is available the schedule can be printed. However, if the configuration is performed by an audio call to a customer service center, printing will not be available, though a schedule can be pushed by over-the-air technology from the customer service center to the parent's phone. If accessing the configuration interface through the touch screen 25, the schedule can be viewed on the screen 25.

Though default priorities (FIG. 39) are provided, preferably an option to set 756 an event priority is also offered to the parent. Setting the event priority allows the CEIL system to prioritize one event over another based on the parent's preference. For example, at 8:00 a.m., a child may be using the smart card system 85 to play animal sounds and animations, but this conflicts with an alert A1 previously set for 8:00 a.m. by the parent. If the A1 alert has a higher priority than the child-selected application, the A1 alert will temporarily interrupt the child-selected application. The child activation systems that the child user of the CEIL system may use to select the child-selected application include the smart card system 85, the touch screen-type display screen 25 or the tactile buttons 21.

FIG. 39 displays default priorities that may be implemented, if not overridden by the parent's preferences. Alerts 760 have the highest priority, with incoming phone calls 762 second, child-selected applications (activities) 764 third, learning activities 766 fourth, entertainment 768 fifth, and so forth.

FIG. 40 displays an exemplary daily schedule 745 as designed by the parent. The parent has scheduled events (learning activities L1, entertainment events E1, E2 and alerts A1, A2) to accommodate the child's routine (in this example, the child is away at preschool from 9 a.m. to noon, so the parent has scheduled no events during that period). Additionally, background monitoring 744, 746 has been scheduled. In this case, the parent has set 744 the GPS system to monitor twenty-four hours a day, and has set 746 the health monitor to monitor during the evening and night.

Thus, through the daily scheduling of events of the various integrated systems, the parent is able to assist the child in planning appropriately for the day, as well as to create and change learning and entertainment events of interest to the child.

The CEIL system may be sold in any of several configurations with different components and functions, as might be appropriate for children of different ages. For example, the doll companion of FIG. 9 may be suitable for children of three to five years, while the doll companion of FIG. 10 may be suitable for infants, and the doll companion of FIG. 11 may be suitable for older children who need only a touch screen. Additionally, the basic doll companion may be sold without the GPS system 60, the health/SIDS system 70, the smart card system 85 and the local audio/visual system 90A, 90B, though the installed software is preferably functional to allow addition of any one or more of these systems. Therefore, at the time of purchase, or at a later date when needed, these systems could be added.

Though generally presented herein with full functionality, a simplified CEIL system without a display screen 25, such as may particularly be designed for an infant, is also within the scope of the invention. The parent is able to use some aspects of the configuration interface, and is able to plan and implement a daily schedule (FIG. 40) of learning and entertainment activities for the child. Some of the learning activities that can be scheduled and executed without a display screen 25 include early alphabet sounds, educational audio books, introduction to various musical styles from Bach to the Beatles, parent voice recordings to maintain voice recognition for the child throughout the day, educational audio books in selected languages, child name recognition and introduction to the sounds, intonation and accents of foreign languages.

From the foregoing, it will be apparent that the doll companion integrating child-directed execution of applications with cell phone communication, education, entertainment, alert and monitoring systems of the current invention allows the child to self-select and to self-execute applications using the integrated system. The cell-phone enabled toy system additionally provides advantages for the parent (monitoring, communication, setting of a child's daily schedule, multiple means of easy access to the configuration interface for updating of the settings and downloaded applications), for the child (learning, entertainment, communication, safety), and for the cell phone provider service (greater market penetration).

Since many modifications, variations and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:
1. A toy device, comprising:
a doll housing having an exterior surface configured with a visually-distinguishable indicator marker, said indicator marker comprising a colored shape, letter, number, or symbol on the exterior surface of the doll body;
a doll computer system disposed within said doll housing, wherein said doll computer system comprises at least one processor-readable storage medium, comprises at least one processor in communication with said at least one processor-readable storage medium, and comprises multiple sets of processor-executable application instructions for executing each of said applications;
a display screen in operational communication with said at least one processor;
an NFC initiator disposed within said doll housing, in signal communication with said at least one processor, and having a radio frequency field-generating portion generating a radio frequency field with said radio frequency field-generating portion disposed directly interior of said indicator marker; and
multiple passive NFC-type tags separate from said doll housing, not connected to a power source, each embedded with a set of application-associated data corresponding to one of said set of processor-executable application instructions on said storage medium; wherein, when one of said NFC-type tags is brought within four centimeters of said indicator marker, said NFC-type tag is powered by said radio frequency field and transmits said set of application-associated data to said NFC initiator;
wherein said at least one processor performs the steps of:
(1.) receiving said transmitted set of application-associated data from said NFC initiator;
(2.) associating said transmitted set of application-associated data from one of said tags with one of said processor-executable application instructions on said storage medium; and

(3.) executing the corresponding one of said processor-executable application instructions based on receipt of said transmitted set of application-associated data.

2. The toy device, as recited in claim 1, wherein:
said display screen consists of a touch screen comprising a touch-sensitive surface for receiving touch input data related to a location on said touch-sensitive surface.

3. The toy device as recited in claim 1, wherein said NFC initiator operates at the 13.56 MHz radio band.

4. The toy device, as recited in claim 1, wherein:
said doll/toy computer system further comprises processor-executable cellular system software instructions; and
said at least one processor performs the further steps of:
(4.) executing and utilizing said cellular system software instructions to send and receive at least one of cellular data transmissions and cellular voice transmissions.

5. The toy device, as recited in claim 1, further comprising at least one tactile button accessible from the exterior of said doll housing, wherein said at least one processor performs the further steps of:
(4.) receiving a tactile input signal created by actuation of said at least one tactile button; and
(5.) utilizing said tactile input signal as an input into said processor-executable application instructions.

6. The toy device as recited in claim 1 wherein said at least one processor performs the further steps of:
(4.) establishing wireless communication with a configuration interface server;
(5.) receiving from said configuration interface server a time schedule for execution of a particular one of said processor-executable applications; and
(6.) executing said particular one of said processor-executable application instructions based on said time schedule.

7. The toy device as recited in claim 1, further comprising:
a camera operable to record video images and operably connected to said at least one processor, wherein said camera is oriented directing a lens of said camera outward from said doll/toy housing;
at least one speaker operable to provide auditory output and operably connected to said at least one processor; and
a microphone operable to record auditory input and operably connected to said at least one processor.

8. The toy device as recited in claim 1, further comprising a health wireless radio frequency receiver and a health monitoring system, wherein said health monitoring system comprises a wireless radio frequency transmitter and at least one health parameter sensor, wherein said health parameter sensor comprises at least one of a sound sensor, a movement sensor, a weight sensor, a carbon dioxide sensor, a temperature sensor, a respiratory rate sensor, and an acceleration sensor.

9. The toy device as recited in claim 4, further comprising:
a GPS receiver disposed within said doll/toy housing that performs the steps of receiving GPS satellite signals, creating location data based on at least said GPS satellite signals, and transmitting said location data to said at least one processor;
a safety band separable from said doll companion device; wherein said safety band comprises a tamper-resistant closure and a wireless data transmitter for transmitting safety band wireless data; and
a wireless data receiver disposed within said doll/toy housing and in signal communication with said at least one processor; wherein said wireless data receiver performs the steps of receiving said safety band wireless data and conveying said safety band wireless data to said at least one processor; wherein said at least one processor performs the further steps of:
(5.) receiving said safety band wireless data;
(6.) determining a separation of said safety band from said doll housing based on the reception of said wireless data or the lack of reception of said wireless data; and
(7.) utilizing said cellular system software instructions to transmit an alert notification based on said determined separation to at least one remote adult user phone.

10. The toy device, as recited in claim 1, wherein said at least one processor performs the further steps of:
(4.) establishing wireless communication with an administrative interface server;
(5.) transmitting, via said wireless communication system, data based on said transmitted set of application-associated data to said administrative interface server; and
(6.) receiving from said administrative server, via said wireless communication in response to said data based on said transmitted set of application-associated data, a downloaded new set of said processor-executable application instructions.

11. The toy device, as recited in claim 4, wherein said cellular data transmissions comprise a
downloaded new set of said processor-executable application instructions.

12. The toy device, as recited in claim 1, wherein:
said at least one processor performs the further steps of:
(4.) establishing wireless communication with an application server; and
(5.) initiating download of at least one of content and said processor-executable application instructions from said application server triggered by the receipt of said transmitted set of application-associated data.

13. The toy device, as recited in claim 1, wherein:
each of said passive NFC-type tags comprises an externally-disposed, user-viewable image that has a correspondence to said first one of said processor-executable application instructions.

\* \* \* \* \*